(12) United States Patent
Kim et al.

(10) Patent No.: US 8,288,378 B2
(45) Date of Patent: Oct. 16, 2012

(54) PHOSPHOINOSITIDE MODULATION FOR THE TREATMENT OF NEURODEGENERATIVE DISEASES

(75) Inventors: Tae-Wan Kim, East Brunswick, NJ (US); Gilbert Di Paolo, Northford, CT (US); Min Suk Kang, Fort Lee, NJ (US); Diego Berman, New York, NY (US); Laura Beth Johnson McIntire, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 12/467,583

(22) Filed: May 18, 2009

(65) Prior Publication Data

US 2010/0035811 A1   Feb. 11, 2010

Related U.S. Application Data

(63) Continuation of application No. PCT/US2007/085274, filed on Nov. 20, 2007.

(60) Provisional application No. 60/860,075, filed on Nov. 20, 2006, provisional application No. 60/970,812, filed on Sep. 7, 2007.

(51) Int. Cl.
  *A61K 31/122*  (2006.01)
  *A61K 31/13*   (2006.01)
  *A61K 31/382*  (2006.01)
  *A61K 31/385*  (2006.01)
  *A61K 31/435*  (2006.01)
  *A61P 25/28*   (2006.01)

(52) U.S. Cl. ............... 514/231.5; 514/224.5; 514/229.8; 514/231.2; 514/232.8; 514/436; 514/451; 514/453

(58) Field of Classification Search ............ 514/12, 514/674, 2, 44 A, 224.5, 229.8, 231.2, 231.5, 514/232.8, 436, 451, 453
See application file for complete search history.

(56) References Cited

U.S. PATENT DOCUMENTS 7,049,313 B2 *  5/2006  Smith et al. ............ 514/231.5
2004/0092561 A1 *  5/2004  Ruckle et al. ............ 514/369

FOREIGN PATENT DOCUMENTS

WO   WO 2004/029055   *   8/2004

* cited by examiner

*Primary Examiner* — Shengjun Wang
*Assistant Examiner* — Sahar Javanmard
(74) *Attorney, Agent, or Firm* — Baker Botts L.L.P.

(57) ABSTRACT

The present invention relates to the use of agents that inhibit the toxic effects of amyloid oligomers by increasing intracellular levels of phosphoinositol 4-phosphate (PI(4)P, or "PIP") and/or phosphotidylinositol 4,5-biphosphate (PI(4,5)P2 or "PIP2"), the use of such agents for the treatment of neurodegenerative diseases, methods of treating neurodegenerative diseases by administration of agents which alter lipid metabolism, and methods of identifying agents which alter the association of presenilins with γ-secretase and lipid rafts.

1 Claim, 27 Drawing Sheets

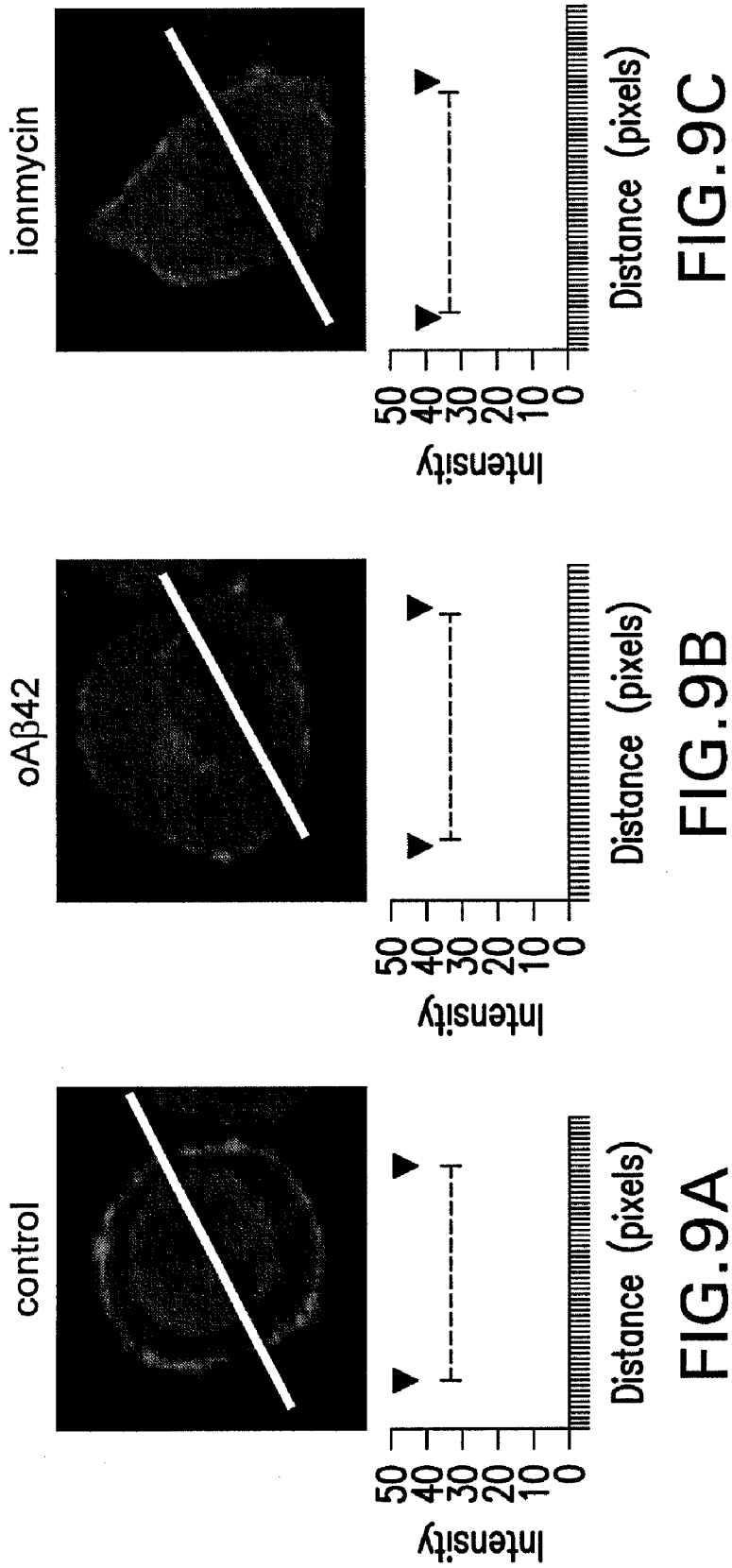

Figure 1:
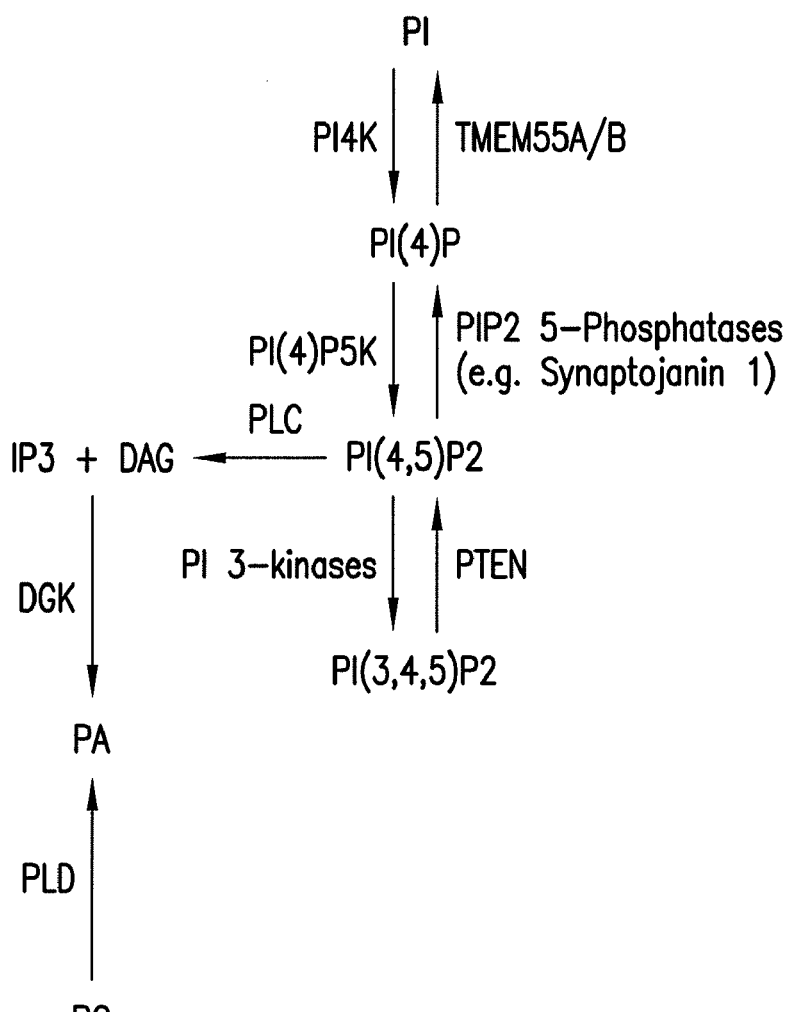

| Kinase | IC$_{50}$ Values ($\mu M$) | Kinase | IC$_{50}$ Values ($\mu M$) |
|---|---|---|---|
| PI3Ks | | PIKKs | |
| p110$\alpha$ | 3.3 | ATR | 20 |
| p110$\beta$ | 1.2 | ATM | 0.005 |
| p110$\delta$ | 0.72 | DNA-PK | 10 |
| p110$\gamma$ | 9.9 | mTORC1 | 20 |
| PI3KC2$\alpha$ | ND | mTORC2 | >100 |
| PI3KC2$\beta$ | ND | PIPKs | |
| PI3KC2 | ND | PI4P5KI$\alpha$ | >100 |
| hsVPS34 | 10 | PI4P5KI$\beta$ | >100 |
| PI4Ks | | PI4P5KII$\beta$ | ND |
| PI4KII$\alpha$ | >100 | | |
| PI4KIII$\alpha$ | >100 | | |
| PI4KIII$\beta$ | >100 | | |

FIG.22

PHOSPHOINOSITIDE MODULATION FOR THE TREATMENT OF NEURODEGENERATIVE DISEASES

CROSS-REFERENCE TO RELATED APPLICATIONS

This application is a continuation of International Application No. PCT/US2007/085274, filed Nov. 20, 2007, and published on May 29, 2008 as International Publication No. WO/2008/064244, which claims priority to U.S. Provisional Application Ser. No. 60/860,075, filed Nov. 20, 2006 and U.S. Provisional Application Ser. No. 60/970,812, filed Sep. 7, 2007, each of which is hereby incorporated by reference in their entireties.

GRANT INFORMATION

The subject matter of this application was developed at least in part using National Institutes of Health Grant Nos. AT001643, NS43467, NS056049 and HD047733, so that the United States Government holds certain rights herein.

1. INTRODUCTION

The present invention relates to agents that inhibit the toxic effects of amyloid oligomers by increasing intracellular levels of phosphoinositol 4-phosphate (PI(4)P, or "PIP") and/or phosphotidylinositol 4,5-biphosphate ("PI(4,5)P2" or "PIP2"), assays for identifying such agents, and the use of such agents for the treatment of neurodegenerative diseases, in particular Mild Cognitive Impairment and Alzheimer's Disease.

2. BACKGROUND OF THE INVENTION

2.1 Neurodegenerative Diseases

Neurodegenerative diseases encompass a variety of disorders characterized by synaptic dysfunction, associated with a progressive decline in cognitive and functional abilities, often resulting in death. Alzheimer's disease (AD) is the most common age-associated debilitating neurodegenerative disorder, affecting approximately 4 million Americans and about 20-30 million people worldwide. The classical neuropathological features of AD include the presence of senile (β-amyloid-containing) plaques and neurofibrillary tangles (4) in the hippocampus, the amygdala, and the association cortices of the temporal, frontal and parietal lobes. More subtle changes include reactive astrocytic changes, as well as the loss of neurons and synapses in the entorhinal cortex and basal forebrain.

2.2 Presenilins and Familial Alzheimer's Disease

About five percent of AD cases are familial (FAD) and inherited by autosomal dominant mutations in APP and the presenilins (PS1 and PS2). Although some FAD cases occur due to mutations in amyloid precursor protein (APP) itself, more than half of FAD cases and the most aggressive forms of FAD (with onset typically occurring at 40-50 years of age but rarely developing in the second or third decade of life) are attributable to missense mutations in the PS1 gene, with more than 140 mutations identified thus far (1-3). The presenilins are multipass transmembrane proteins that localize predominantly to the endoplasmic reticulum (ER) and other intracellular compartments, with a small pool present at the plasma membrane (5,6). PS is initially synthesized as a 42-43 kDa holoprotein that undergoes proteolytic cleavage within the cytoplasmic loop connecting putative transmembrane segments 6 and 7. This endoproteolytic processing generates stable 27-28 kDa N-terminal and 16-17 kDa C-terminal fragments that combine to form an enzymatically active heterodimer (7-9). Presenilins have two conserved aspartyl residues, a feature of aspartyl proteases, within the PS transmembrane domains 6 and 7 (10) and aspartyl protease transition-state analog inhibitors bind directly to PS1 and PS2 (11,12). Accumulating evidence suggests that the presenilins may serve as catalytic components of the γ-secretase complex, an unconventional aspartyl protease which mediates the cleavage of a growing number of type-1 membrane proteins, including APP.

2.3 Generation of Amyloidogenic Aβ42 Peptide

In the case of APP, γ-secretase mediates the C-terminal cleavage of the amyloid-β(Aβ) domain, thereby liberating Aβ/p3 from membrane-bound APP C-terminal fragments generated through ectodomain shedding by α-(ADAM10 and TACE) or β-secretase (BACE1). γ-secretase cleavage generates two major Aβ isoforms—Aβ40 and Aβ42. It has been well documented (14,15) that all mutations in PS1 and PS2 genes result in modulation of γ-secretase activity, leading to an elevation in the generation of the highly amyloidogenic and neurotoxic Aβ42 species, possibly at the expense of the more benign Aβ40 peptide.

2.4: Aβ Oligomer-Induced Synaptic Dysfunction

Monomeric Aβ undergoes conformational changes to form soluble Aβ oligomers in addition to insoluble fibrils. Mounting evidence indicates that different conformations of Aβ, such as Aβ oligomers and fibrils, may contribute to AD pathogenesis via distinct mechanisms at different stages of the disease [Haass, C. & Selkoe, D. J. (2007). Soluble protein oligomers in neurodegeneration: lessons from the Alzheimer's amyloid beta-peptide. Nat Rev Mol Cell Biol 8, 101-12]. Importantly, accumulation of soluble oligomeric forms of Aβ closely correlates with cognitive decline and/or disease progression in animal models and AD patients [Selkoe D J. Alzheimer's disease is a synaptic failure. Science 298, 789-791; Shankar G. M., Bloodgood B. L., Townsend M., Walsh D. M., Selkoe D. J., Sabatini B. L. (2007) Natural oligomers of the Alzheimer amyloid-beta protein induce reversible synapse loss by modulating an NMDA-type glutamate receptor-dependent signaling pathway. J Neurosci. 27, 2866-75.]. Thus, it is crucial to understand specific and early synaptic/neuronal changes associated with the exposure of neurons to soluble oligomers. The Aβ oligomers, particularly Aβ42, have been shown to directly affect synaptic plasticity and trigger the loss of synaptic dendritic spines, at least in part through their ability to modulate cell surface levels of NMDA and AMPA receptors [Snyder E M, Nong Y, Almeida C G, Paul S, Moran T, Choi E Y, Nairn A C, Salter M W, Lombroso P J, Gouras G K, Greengard P. (2005) Regulation of NMDA receptor trafficking by amyloid-beta. Nat. Neurosci. 8, 1051-1058; Hsieh H, Boehm J, Sato C, Iwatsubo T, Tomita T, Sisodia S, Malinow R. (2006) AMPAR removal underlies Abeta-induced synaptic depression and dendritic spine loss. Neuron 52, 831-43] as well as to affect calcium homeostasis [Demuro A., Mina E., Kayed R., Milton S. C., Parker I., Glabe C. G. (2005). Calcium dysregulation and membrane disruption as a ubiquitous neurotoxic mechanism of soluble amyloid oligomers. J Biol Chem 280, 17294-300].

2.5 Phosphoinositide Signaling and Alzheimer's Disease

Phosphoinositides ("PIs") serve as signaling molecules in a diverse array of cellular pathways (25-27) and aberrant regulation of PIs in certain cell types has been shown to promote various human disease states (47). PI signaling is mediated by the interaction with signaling proteins harboring the many specialized PI-binding domains, including Pleckstrin Homology (PH), epsin N-terminal homology (ENTH), Fabp/YOTB/Vac1p/EEA1 (FYVE), Phox homology (PX), and N-WASP polybasic motif domains (49-54). The interaction between these PI-binding domains and their target PIs results in the recruitment of lipid-protein complex into the intracellular membrane.

PI signaling is tightly regulated by a number of kinases, phosphatases, and phospholipases. A schematic diagram showing the conversions among biologically relevant PIs is presented in FIG. 1. In the central nervous system, the levels of PIs in nerve terminals are regulated by specific synaptic kinases, such as phosphoinositol phosphate kinase type 1γ (PIPk1γ) and phosphatases, such as synaptojanin 1 (SYNJ1). PIP2 hydrolysis in the brain occurs in response to stimulation of a large number or receptors via two major signaling pathways: a) the activation of G-protein linked neurotransmitter receptors (e.g. glutamate and acetylcholine), mediated by PLCβs, and b) the activation of tyrosine kinase linked receptors for growth factors and neurotrophins (e.g. NGF, BDNF), mediated by PLCγ. The reaction produces two intracellular messengers, I(1,4,5)P3 (or "IP3") and diacylglycerol (DAG), which mediate intracellular calcium release and protein kinase C(PKC) activation, respectively. Moreover, localized membrane changes in PIP2 itself are likely an important signal as PIP2 is a known modulator of a variety of channels and transporters (30).

Reduced PI concentration in the temporal cortex of AD patients, as compared to controls, has been reported by Stokes and Hawthorne (63). Quantification studies aimed at comparing the levels of specific PLC isozymes in control and AD brains have reported aberrant accumulation of PLCδ1 and PLC γ1 in AD (31, 32). Studies of agonist-stimulated PIP2 hydrolysis in post-mortem human control and AD brain fractions (33-35) have shown reduced PIP2 hydrolysis in response to cholinergic and serotonergic PLC activation. Several neurotransmitters that act through the PI pathway have been shown to increase APP-α release (64,65), thereby blocking Aβ biogenesis.

2.6 Synaptojanin 1

Synaptojanin 1 belongs to the family of inositol 5-phosphatases, which has ten members. It is the main PIP2-phosphatase in the brain and at the synapse. Its domain structure consists of: (i) a central inositol 5-phosphatase domain that can hydrolyze PIP2 to release phosphate from the 5' position of the inositol ring; (ii) an N-terminal Sac1 region that can also function as a PI phosphatase, although with less selectivity; and (iii) a proline-rich domain (PRD) involved in the binding of SH3 domain-containing proteins, such as endophilin. Although synaptojanin 1 has been mostly implicated in presynaptic trafficking, it is also present at the postsynapse of hippocampal neurons, where it regulates AMPA receptor trafficking and modulates AMPA currents.

2.7 Phosphoinositide 3-Kinases

Phosphoinositide 3-kinases (PI3Ks) are responsible for many intracellular processes including metabolic control, vesicular trafficking, mediation of survival signals and cytoskeleton remodeling (86,87,88). PI3Ks are responsible for the phosphorylation of PIP2 resulting in the formation of phosphatidylinositol (3,4,5) tri-phosphate (PIP3). The production of PIP3 at the plasma membrane results in activation of several downstream signaling pathways as well as the depletion of PIP2.

The PI3K family includes three classes of PI3Ks including catalytic domain containing subunits as well as regulatory subunit adaptor domains. The core catalytic domain of PI3Ks also has high sequence homology to the phosphatidylinositol 4 kinases (PI4Ks) as well as PI3K related protein kinases (PIKKs) (86,87).

The family members of the PI3K and related kinases have recently emerged as important drug targets (86,89). Many early studies relied on two non-selective PI3K inhibitors, wortmannin and LY-294002, which target the entire family of PI3Ks as well as PI3K related protein kinases (PIKKs) and phosphoinositide 4-kinases (PI4Ks) (90). However in recent years isoform specific inhibitors have become available and used to target a variety of pathologies controlled by PI3K signaling pathways. A PI3Kα and mTOR selective inhibitor has been implicated in treatment for glioma (91). PI3Kβ has been selectively inhibited effectively in anti-thrombotic treatments (92). PI3Kδ has been implicated in neutrophil action (93). Finally, PI3Kγ selective inhibitors have been found effective for treatment of mouse models of autoimmune disease (94,95).

Previous studies have implicated PI3Ks and the signaling pathway downstream of PI3Ks in Alzheimer's disease pathology. Post-mortem studies found an activation of the Akt pathway (96-98). However, cells with presenilin mutantations associated with FAD, have deficient PI3K activities (99-101). Interestingly, this deficiency is independent of the secretase activity (102). Presenilin has also been shown to form a complex with and act as a substrate for GSK3 (103, 104). However, this is also independent of secretase activity (105).

PI3K signaling has been shown to be required for APP processing as wortmannin decreased the release of sAPPα and Aβ, resulting in accumulation of intracellular Aβ(106). Additionally, inhibition of GSK3 has been observed to decrease Aβ production (107,108).

3. SUMMARY OF THE INVENTION

The present invention relates to methods of inhibiting the adverse neuronal effects of Aβ42 and to methods of treating neurodegenerative diseases associated with increased levels of Aβ42 by administering agents that increase neuronal levels of phosphoinositol 4-phosphate (PI(4)P, or "PIP") and/or neuronal phosphotidylinositol 4,5-biphosphate ("PIP2") and/or decrease neuronal levels of Aβ42. The present invention further relates to methods of identifying such agents.

In particular groups of embodiments (with reference to FIG. 1), the present invention provides for:

methods of increasing PIP by administering, to a cell or a subject in need of such treatment, an agonist of PI4-kinase, in an amount effective in increasing the level of PIP;

methods of increasing PIP by administering, to a cell or a subject in need of such treatment, an inhibitor of TMEM55A/B, in an amount effective in increasing the level of PIP;

methods of increasing PIP2 by administering, to a cell or a subject in need of such treatment, an agonist of PI(4)P5-kinase, in an amount effective in increasing the level of PIP2;

methods of increasing PIP2 by administering, to a cell or a subject in need of such treatment, an inhibitor of synaptojanin 1, in an amount effective in increasing the level of PIP2;

methods of increasing PIP2 by administering, to a cell or a subject in need of such treatment, an inhibitor of PI3-kinase, in an amount effective in increasing the level of PIP2;

methods of increasing PIP2 by administering, to a cell or a subject in need of such treatment, an inhibitor of ataxia-telangiectasia-mutated (ATM) kinase, in an amount effective in increasing the level of PIP2;

methods of increasing PIP2 by administering, to a cell or a subject in need of such treatment, an agent which decreases levels of phosphatidic acid (PA); and methods of reducing the amount of presenilin-1 C-terminal fragment associated with a lipid raft.

In additional non-limiting embodiments, the present invention provides for assays to (i) identify agents which increase PIP2 and/or inhibit Aβ42 toxicity using a PIP2 sensor; (ii) identify agents that inhibit synaptojanin-1; and (iii) identify agents which reduce the amount of presenilin-1 C terminal fragment associated with a lipid raft.

4. BRIEF DESCRIPTION OF THE FIGURES

FIG. 1. Regulation of phosphoinositide (PI) metabolism. Representative enzymes that mediate phosphorylation (kinases include PI4K, PI(4)P5K, PI 3-kinases, and DGK) and dephosphorylation (phosphatases include TMEM55A/B, PIP2 5-Phosphatases such as synaptojanin 1, and 3-phosphatases such as PTEN) are also shown. Phospholipases include PLC. Phosphoinositides are phosphorylated derivatives of the minor membrane phospholipid phosphatidylinositol (PI). A series of PI kinases and phosphates mediate inter-conversion between different PI species, including PI(4)P (PIP), PI(4,5)P2 (PIP2), and PI(3,4,5)P3 (PIP3). Phospholipase C (PLC) mediates hydrolysis of PI(4,5)P2 to generate second messengers IP3 and DAG. Phosphatidic acid (PA) can be generated either from diacylglycerol (DAG) by DGK (DAG kinases) or from phosphatidlycholine (PC) by phospholipase D (PLD).

Figure 2A:
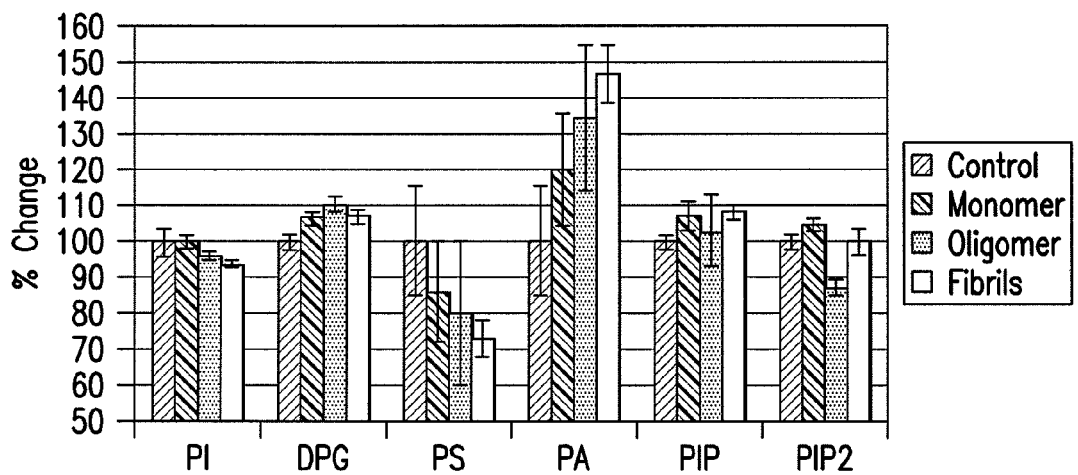
Figure 2B:
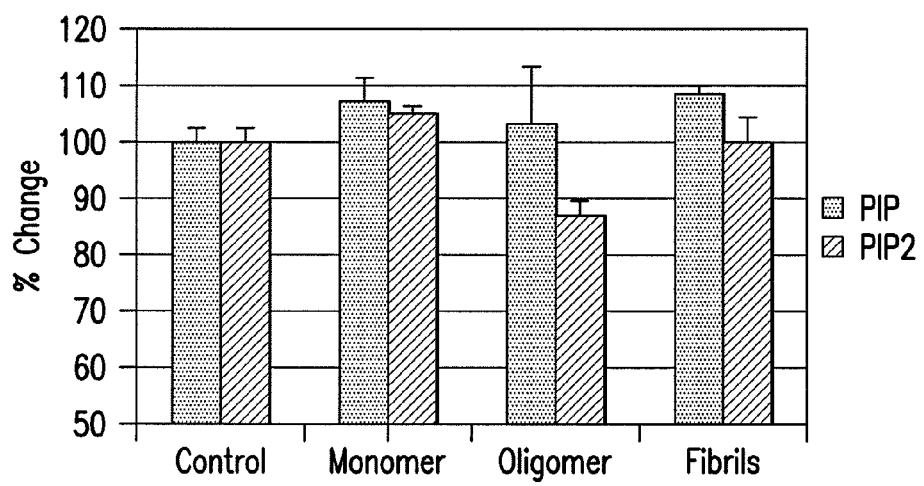
Figure 2C:
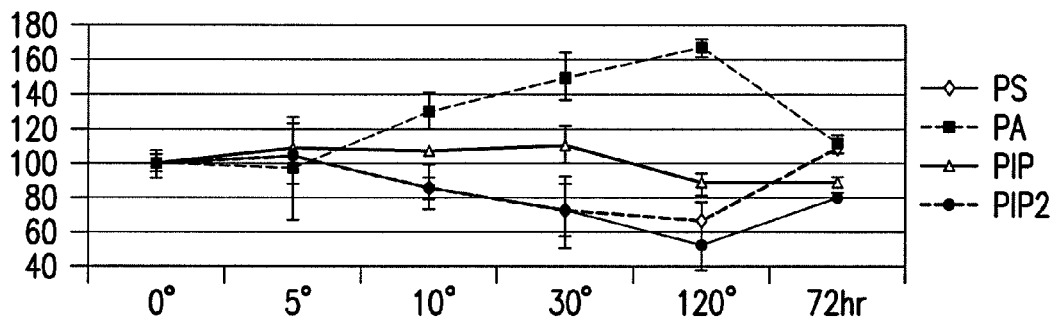

FIG. 2A-C. Treatment of cultured neurons with oligomeric forms of Aβ42 peptide. (A and B) Oligomeric forms of Aβ42 leads to reduced PIP2 levels and increases in PA levels. (C) Percent change of PS, PA, PIP, and PIP2 levels over time.

Figure 3A:
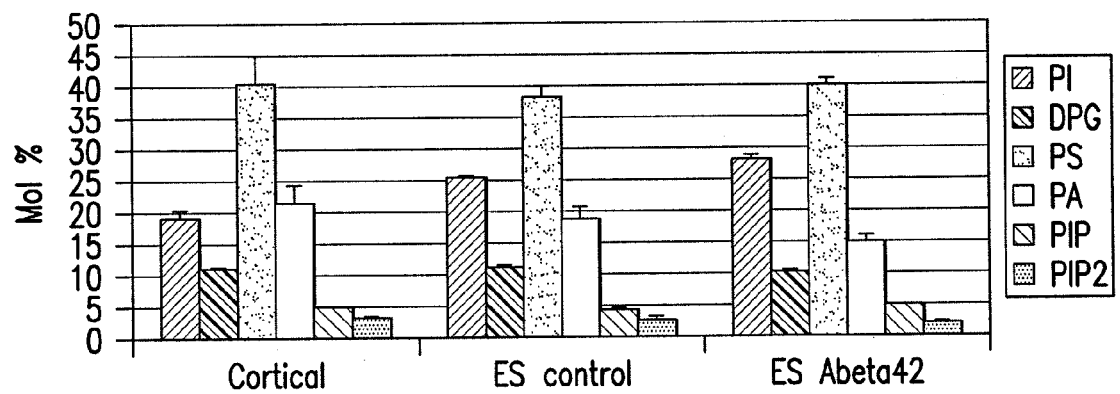
Figure 3B:
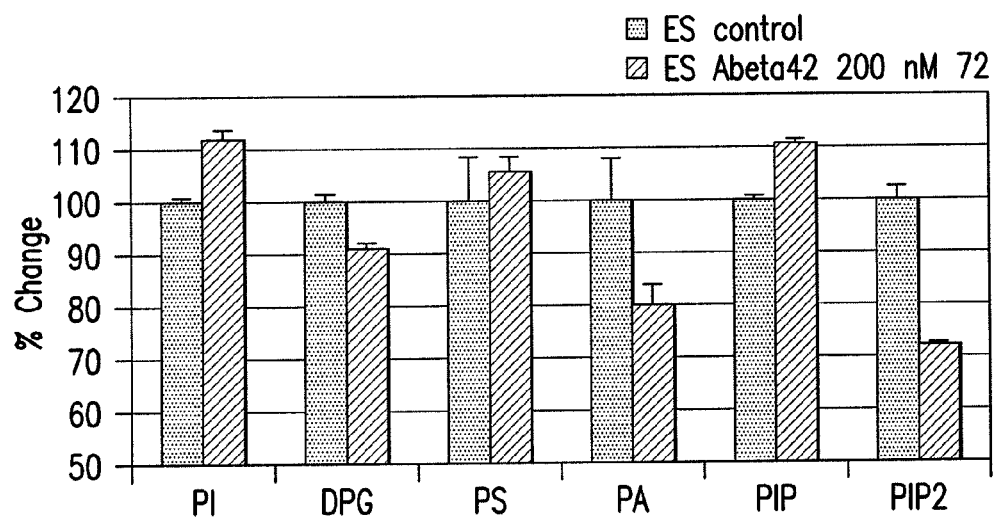

FIG. 3A-B. Effect of Aβ42 on the lipid profile of neurons derived from ES cells. (A) No differences in lipid profiles (expressed as mol %) were found between cortical neurons from wild-type mice and neurons derived from ES cells. (B) Oligomeric Aβ42 also lowers PIP2 levels in ES-derived neurons.

FIG. 4A-E. Effects of Aβ42 on phosphoinositide levels in various cell types. (A) Effect of Aβ42 on primary cultures of murine cortical neurons on levels of DPG, phosphatidic acid ("PtdA"), PIP and PIP2. (B) Experiments as for part (A), further testing the effects of the inverse sequence (Aβ42Rev), a preparation of the shorter and non-cytotoxic Aβ peptide, Aβ38, which was processed similarly to oligomeric Aβ42, and antibody 6E10 (directed to the first 17 amino acids of Aβ42). (C) Effect of Aβ produced naturally from cells expressing the "Swedish" mutant of APP (swAPP) on PIP2 levels in cortical neurons from a transgenic mouse expressing the swAPP mutant. (D) Effect of Aβ produced naturally from cells expressing the "Swedish" mutant of APP (swAPP) on PIP2 levels in N2a neuroblastoma cells expressing the swAPP mutant. (E) Comparison of the effects of oligomeric Aβ42 on neuronal PIP2 levels in the presence of Ca2+ ionophore or chelator indicated that Aβ42-induced PIP2 deficiency is Ca+−dependent.

Figure 5A:
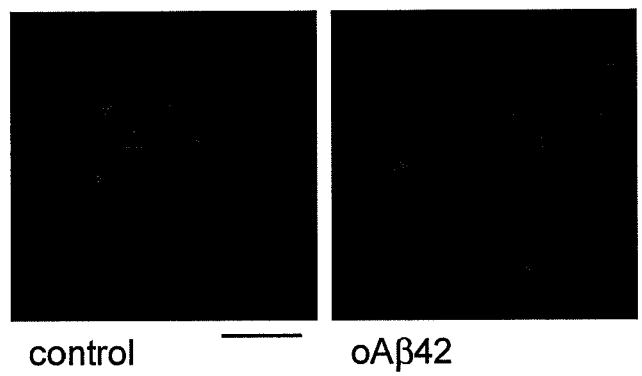
Figure 5B:
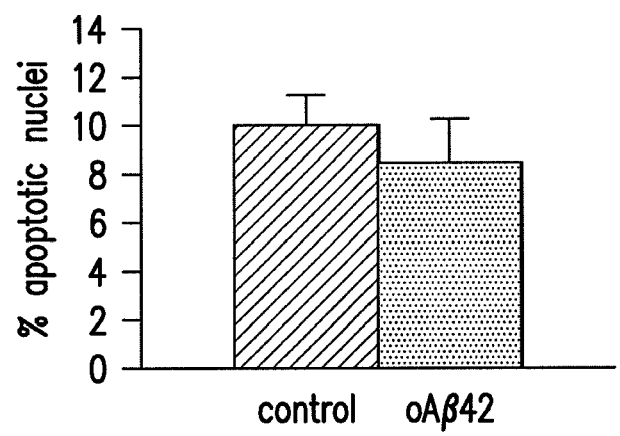
Figure 5C:
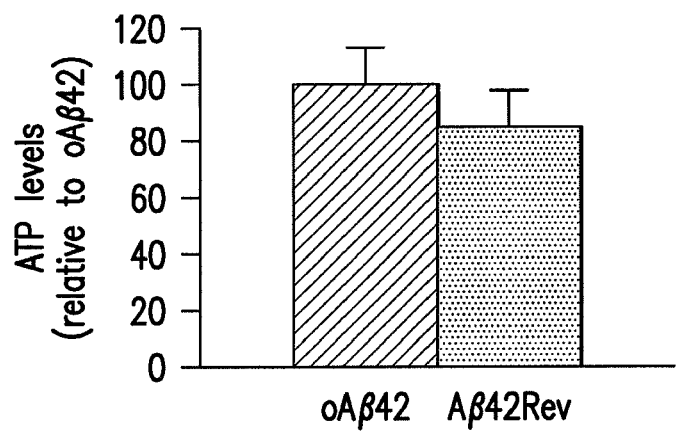

FIG. 5A-C. (A) Pyknosis in neurons treated with either vehicle (control) or oligomeric Aβ42 after 3 days. (B) Percent of apoptotic nucleic associated with control or oAβ42-treated neurons. (C) ATP levels in neurons treated with oAβ42 or Aβ42rev.

Figure 6:
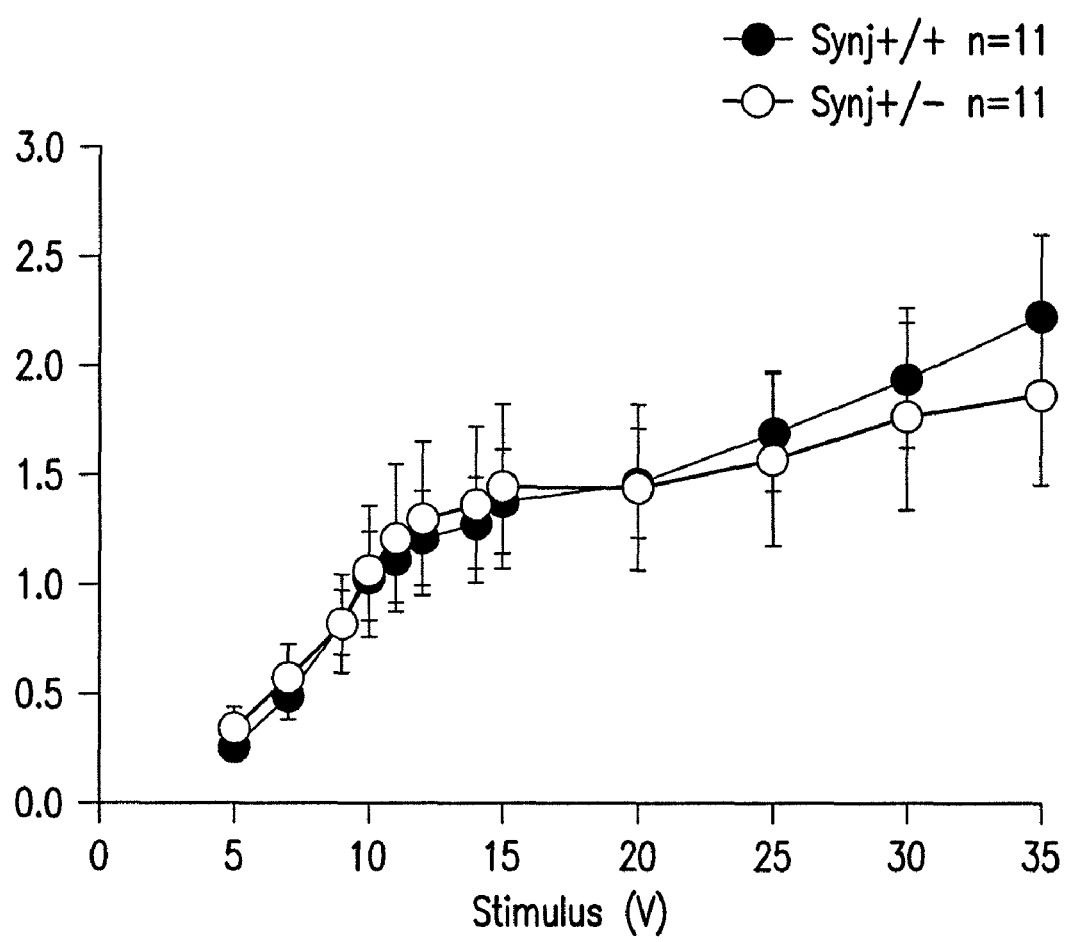

FIG. 6. fEPSP (fast Excitatory Post-Synaptic Potential) (V/s) in response to increasing voltage in mice wild-type for Synj1 (Synj1$^{=/+}$) and heterozygous for a knock-out mutation (Synj1$^{+/-}$).

Figure 7:
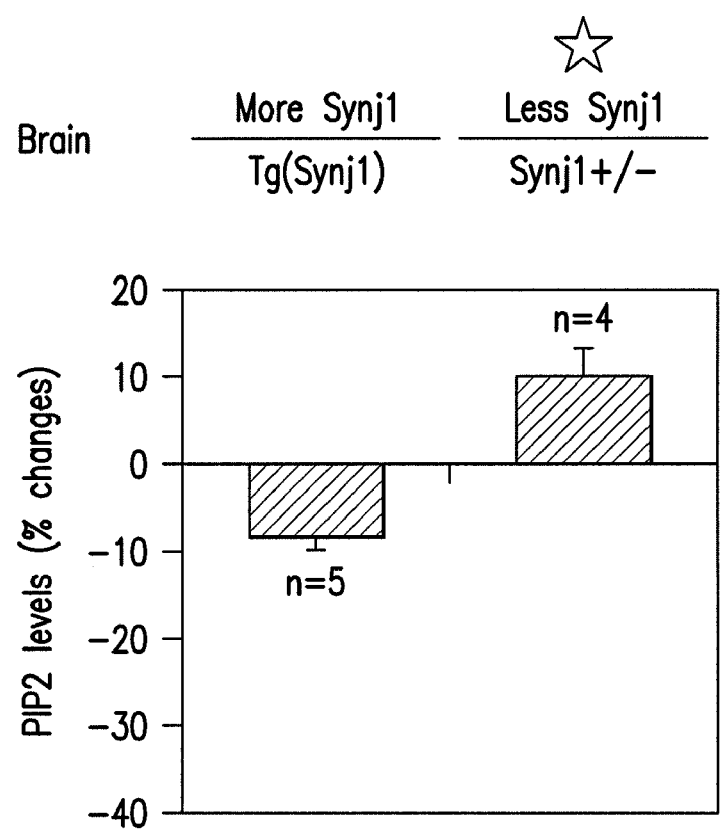

FIG. 7. Levels of PIP2 in Tg(Synj1) mice, which overexpress Synj1 and are a model for Down's Syndrome, and in Synj1$^{+/-}$ knock-out heterozygotes.

Figure 8A:
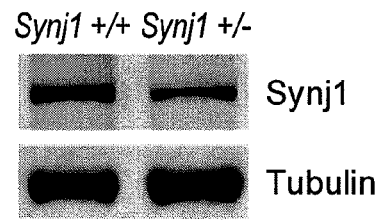
Figure 8B:
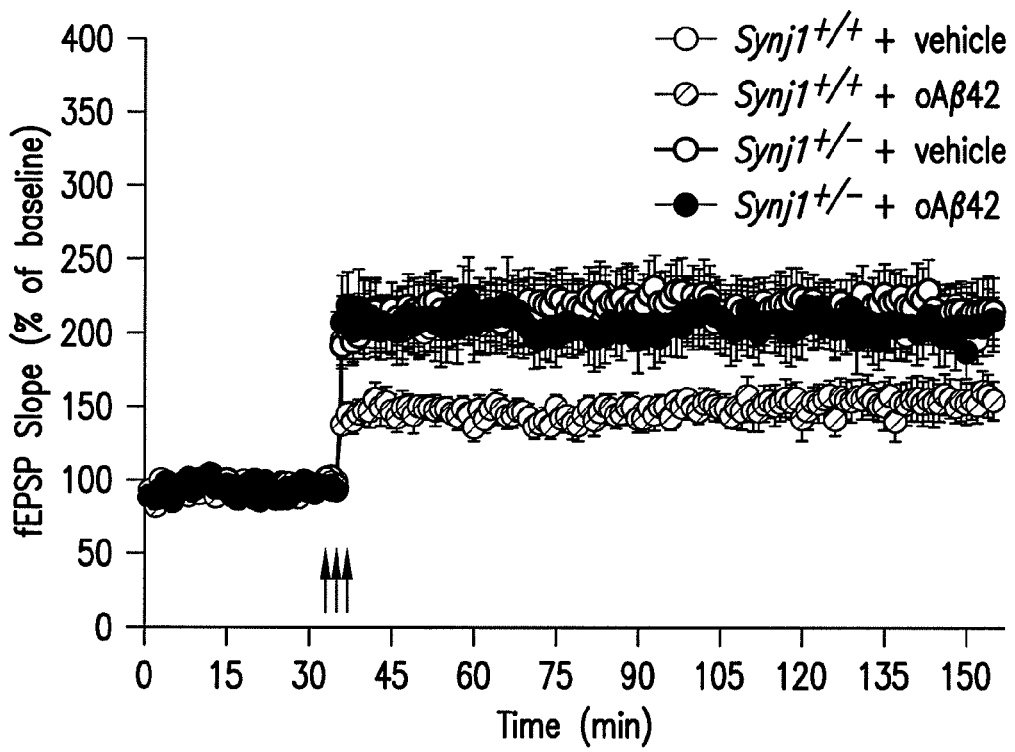
Figure 8C:
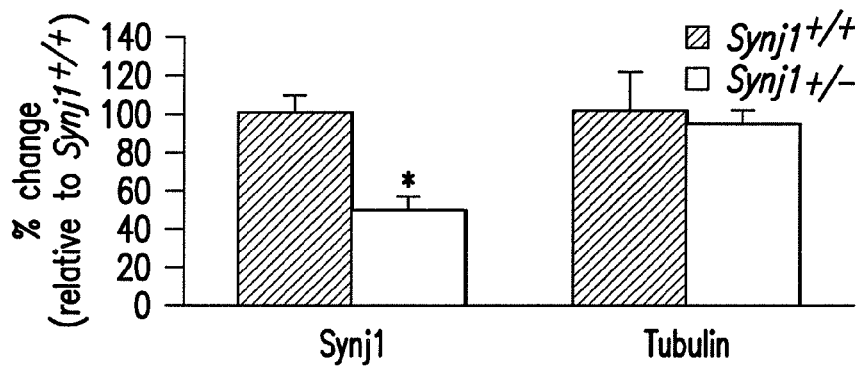

FIG. 8A-C. (A) Western blot showing relative levels of Synj1 in Synj1$^{+/+}$ and Synj1$^{+/-}$ mice, with tubulin used as a control. (B) Percent change in PIP2 levels in Synj1$^{+/+}$ and Synj1$^{+/-}$ mice. (C) LTP in Synj1$^{+/+}$ and Synj1$^{+/-}$ mice in the presence and absence of oAβ42.

FIG. 9A-E. Epifluorescence microscopy of PC12 cells carrying a PH-GFP sensor for PIP2, showing (A) negative control cell; (B) cell treated with oAβ42; and (C) cell treated with ionomycin. (D) Percent change in plasma membrane/cytoplasmic probe localization for cells treated with oAβ42, ionomycin, or Aβ42Rev. The dotted line indicates the negative control (a 100 percent value indicates no change in signal). E. Percent change in plasma membrane/cytoplasmic probe localization in PC12/PH-GFP cells which were either untreated (control), treated with oAβ42, treated with oAβ42 in the presence of PLC inhibitor U73122, treated with oAβ42 in the presence of edelfosine, or treated with U73122 or edelfosine alone.

FIG. 10A-F. (A) Structure of (20S)Rg3. (B) (20S)Rg3 effect on various phosphoinositide-related molecules. (C) (20S)Rg3 enhances the activity of PI4KIIa, but not the "dead kinase" counterpart, in a kinase assay. (D) graphical representation of (C). (E) Dose-response effect of (20S)Rg3 on PI4K activity. (E) GST-PIPK1γ activity in the presence and absence of (20S)Rg3.

Figure 11A:
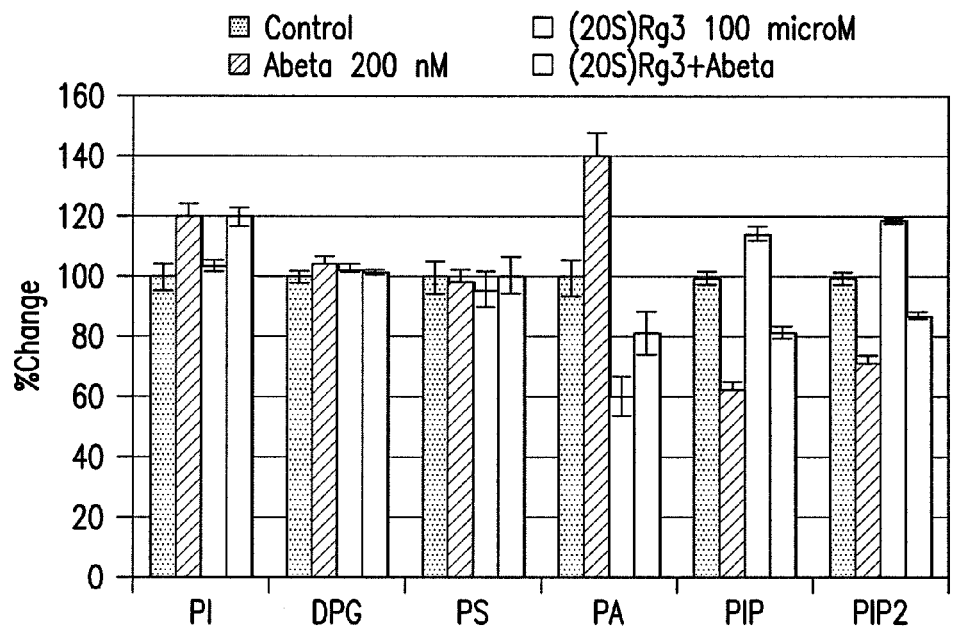
Figure 11B:
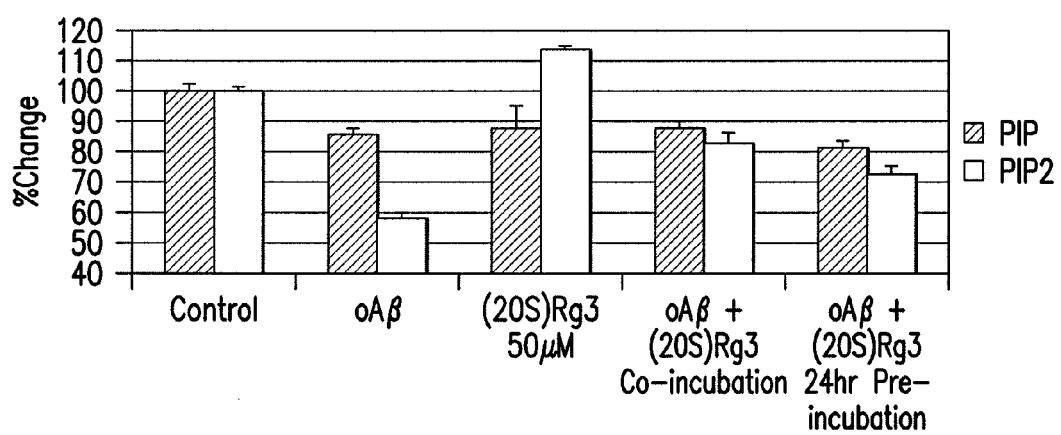

FIG. 11A-B. (20S)Rg3 reverses the effects of Aβ42. (A) Treatment with (20S)Rg3 inhibited the reduction of PIP2 by Aβ42. (B) Co-incubation of (20S)Rg3 and Aβ42 oligomers, as well as preincubation of (20S)Rg3 with subsequent addition of Aβ42 oligomers blocks Aβ42 oligomer induced PIP2 reduction.

Figure 12A:
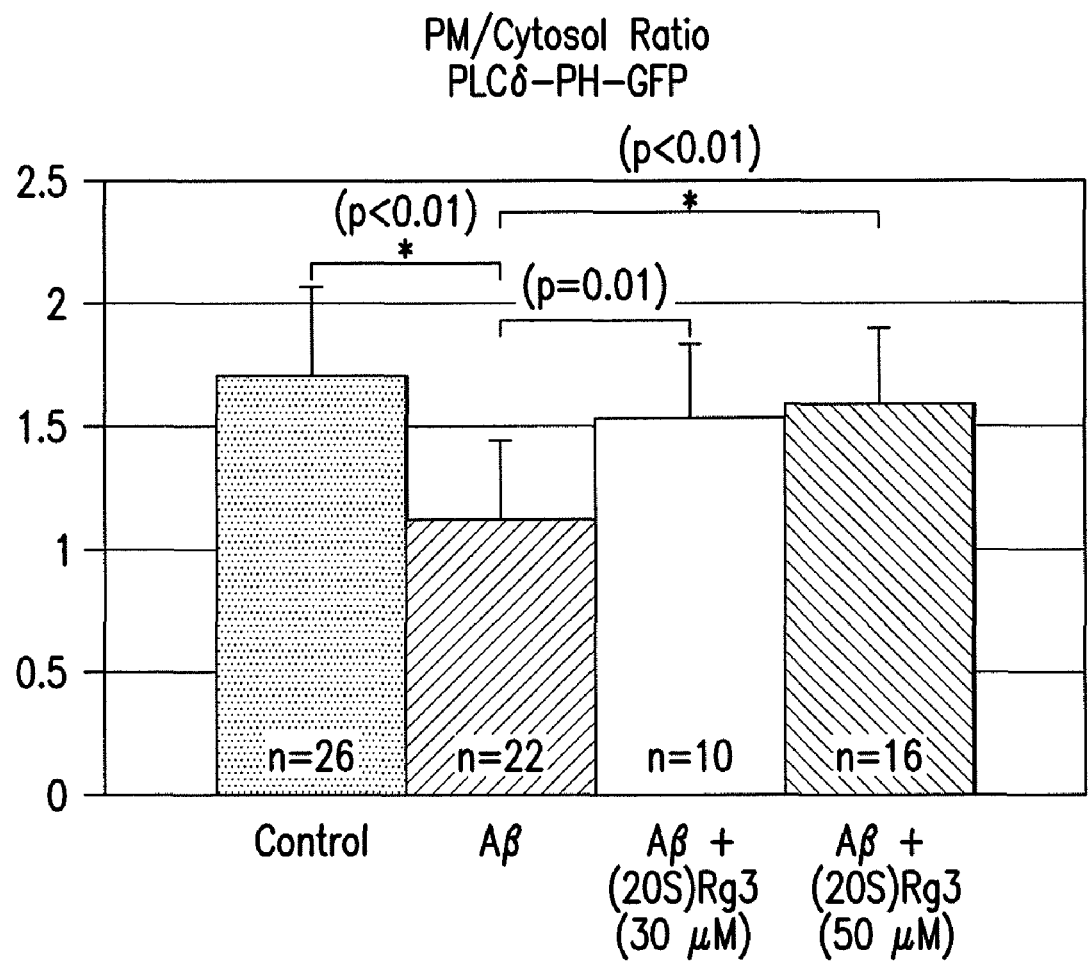
Figure 12B:
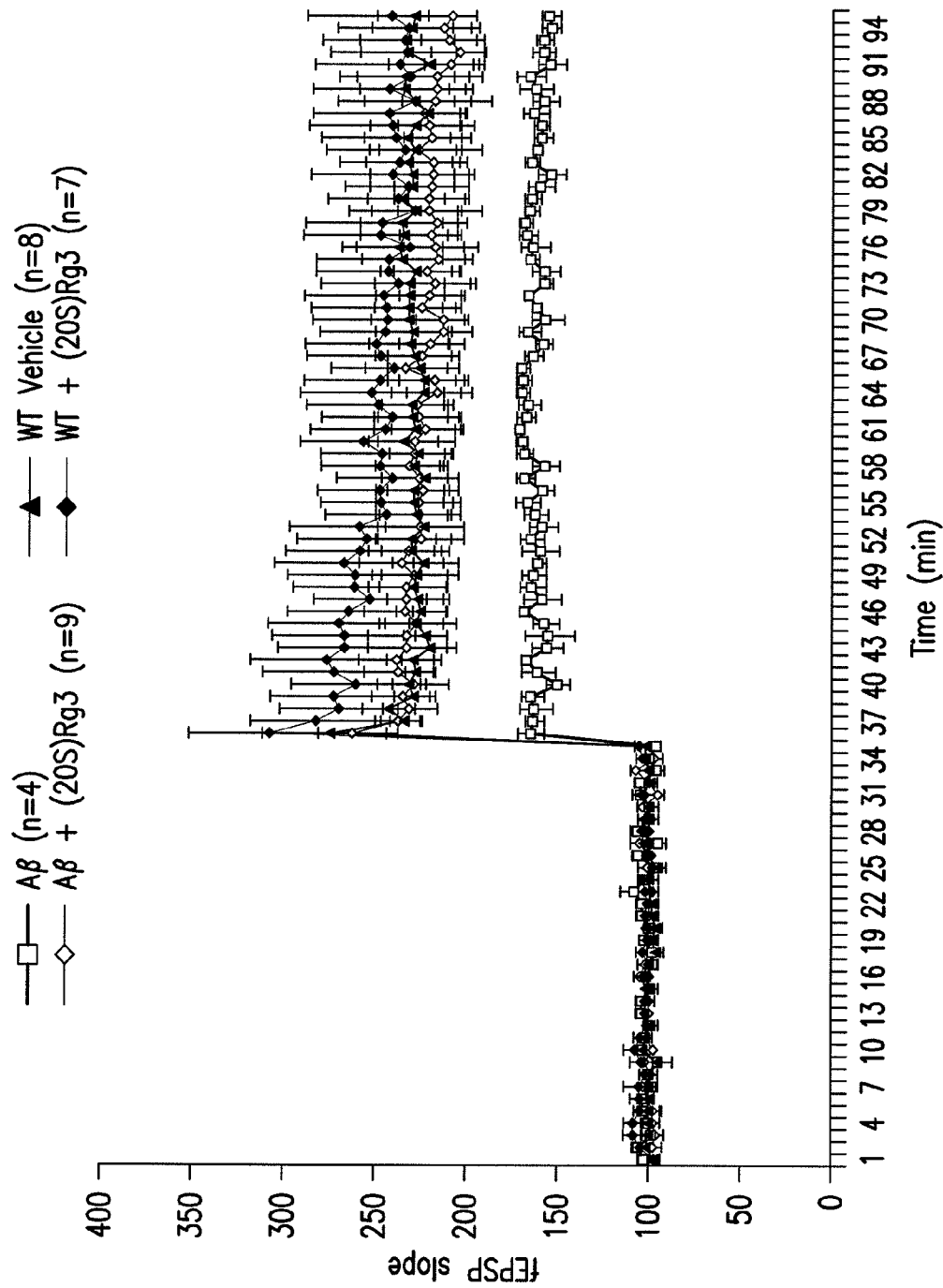
Figure 12C:
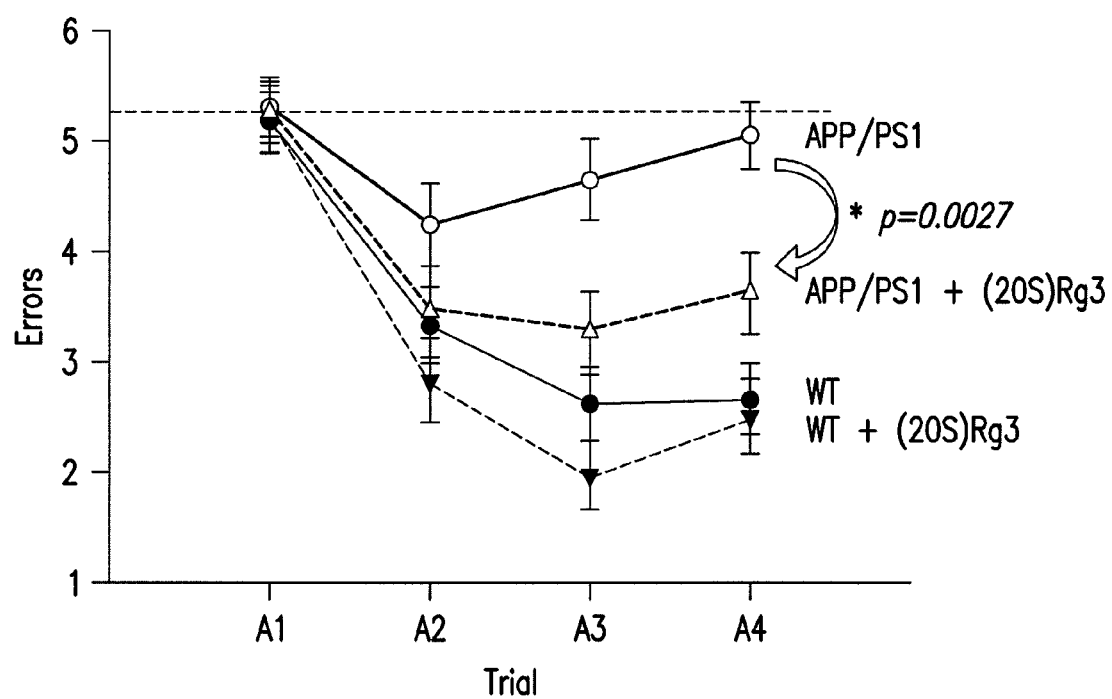

FIG. 12A-C. (A) Plasma membrane to cytosol ratio of GFP-PH$_{PLC\delta1}$ sensor in control cells as compared to cells treated with oAβ42 alone or in conjunction with 30 μM or 50 μM (20S)Rg3. (B) LTP in neurons which were either untreated, treated with oAβ42, treated with (20S)Rg3, or treated with both oAβ42 and (20S)Rg3. (C) Memory errors in APP/PS1 mutant mice relative to wild type and compared to wild-type or mutant mice treated with (20S)Rg3.

Figure 13A:
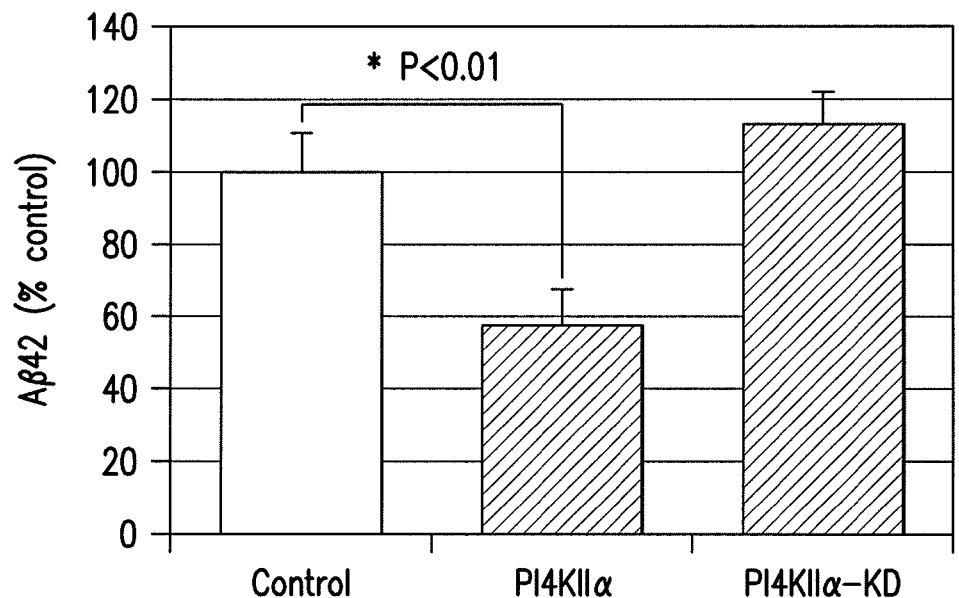
Figure 13B:
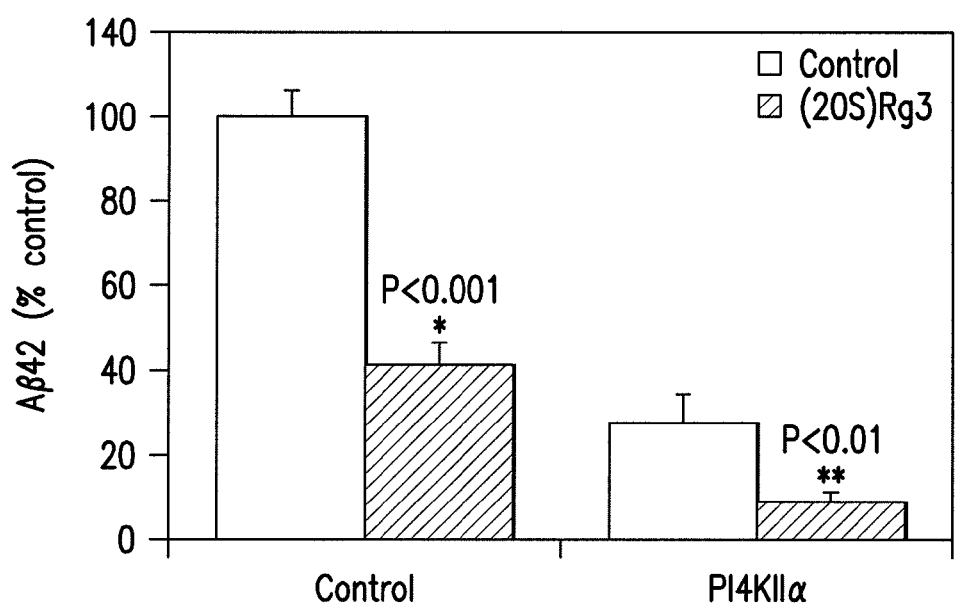

FIG. 13A-B. (A) Percent control Aβ42 in CHO cells overexpressing PI4KIIα or the corresponding "dead kinase". (B) Effect of (20S)Rg3 on percent control Aβ42 levels in control cells and in cells overexpressing PI4KIIα.

FIG. 14A-F. Neuronal staining to compare differentiation and morphology of stained wild-type pyramidal neurons (A) with differentiated murine embryonic stem cell-derived pyramidal neurons which are heterozygous for a knock-out mutation of PI4KIIα ("PI4KIIα$^{+/-}$") (B). (C) Western blot showing PI4KIIα expression in wild-type and PI4KIIα$^{+/-}$ neurons. (D) Kinase activity in wild-type and PI4KIIα$^{+/-}$ neurons. (E)

PIP levels in wild-type and PI4KIIα$^{+/-}$ neurons. (F) Aβ42 levels in wild-type and PI4KIIα$^{+/-}$ neurons.

FIG. 15A-E. (A) Lipid raft fractionation experiments showing the distribution of full-length PS1 ("PS1-FL"), PS1 C-terminal fragment ("PS1-CTF"), PI4KIIα, and flotillin-1 in control cells, cells treated with (20S)Rg3, and PI4KIIα-overexpressing cells. (B) Western blot showing the amounts of PS1-CTF, PI4KIIα, full length APP ("APP-FL") and APP C terminal fragment ("APP-CTF") in control cells and cells treated with (20S)Rg# or PI4KIIα-overexpressing cells. (C) Graphical representation of the results in (B) for PS1-CTF. (D) levels of sAPPα and sAPPβ in control and PI4KIIα-overexpressing cells. (E) Results of cross-linking and immunoprecipitation showing PS1-PI4KIIα complex.

Figure 16A:
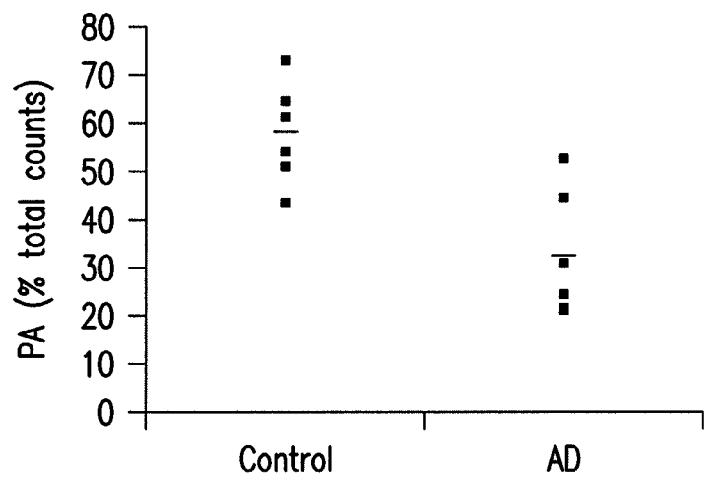
Figure 16B:
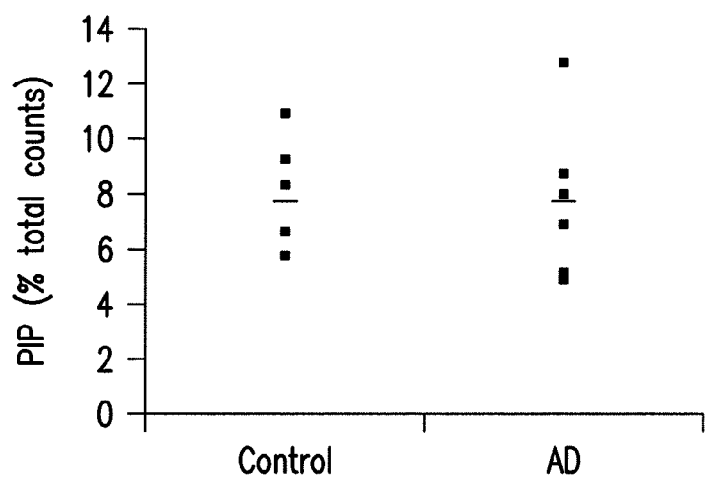
Figure 16C:
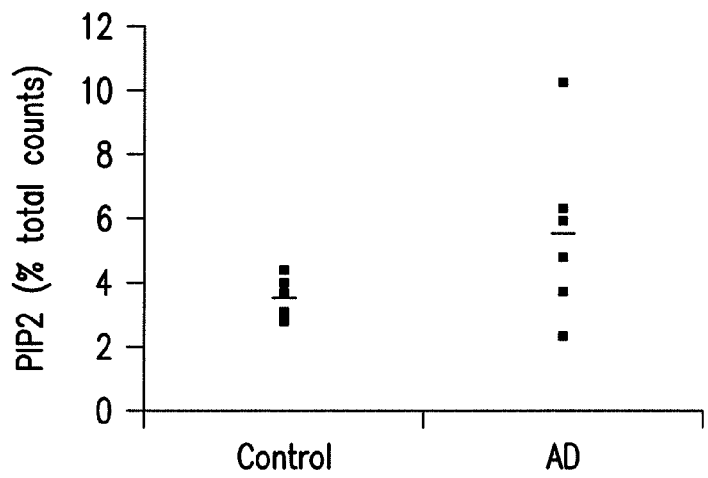

FIG. 16A-C. Altered phosphoinositide metabolism in the brains of AD patients. (A) Measurement of phosphatidic acid (PA). (B) Measurement of PIP. (C) Measurement of PIP2.

Figure 17:
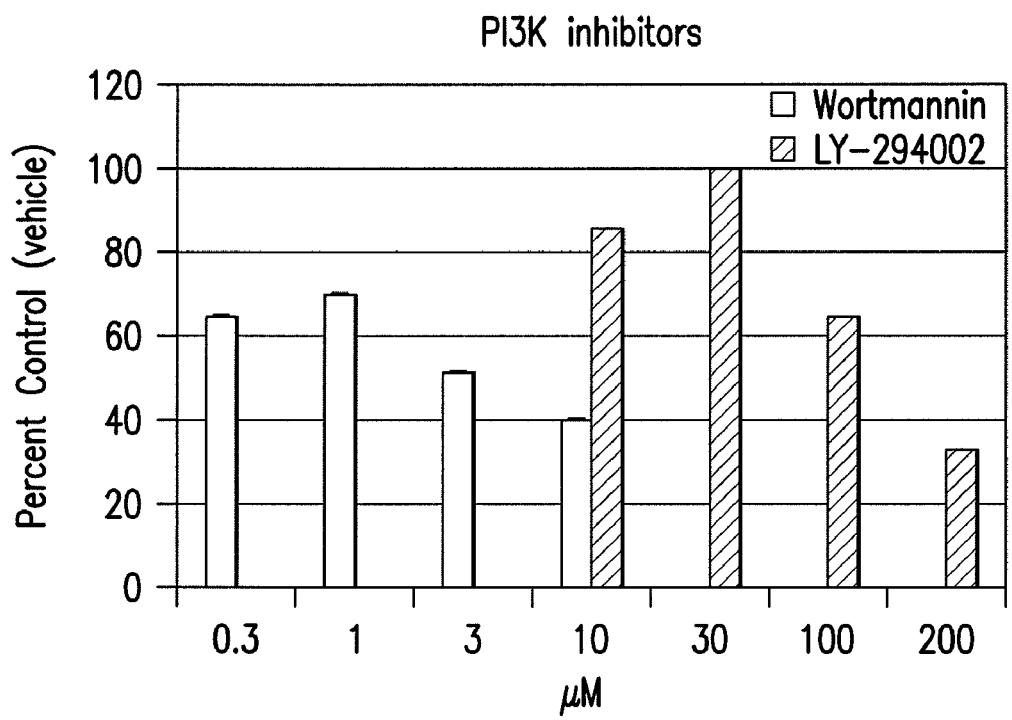

FIG. 17. Change in Aβ42 levels (percent control) in N2a cells stably expressing human APP with the Swedish mutation treated with various concentrations of the pan PI3Kinase inhibitors wortmannin and LY-294002.

Figure 18:
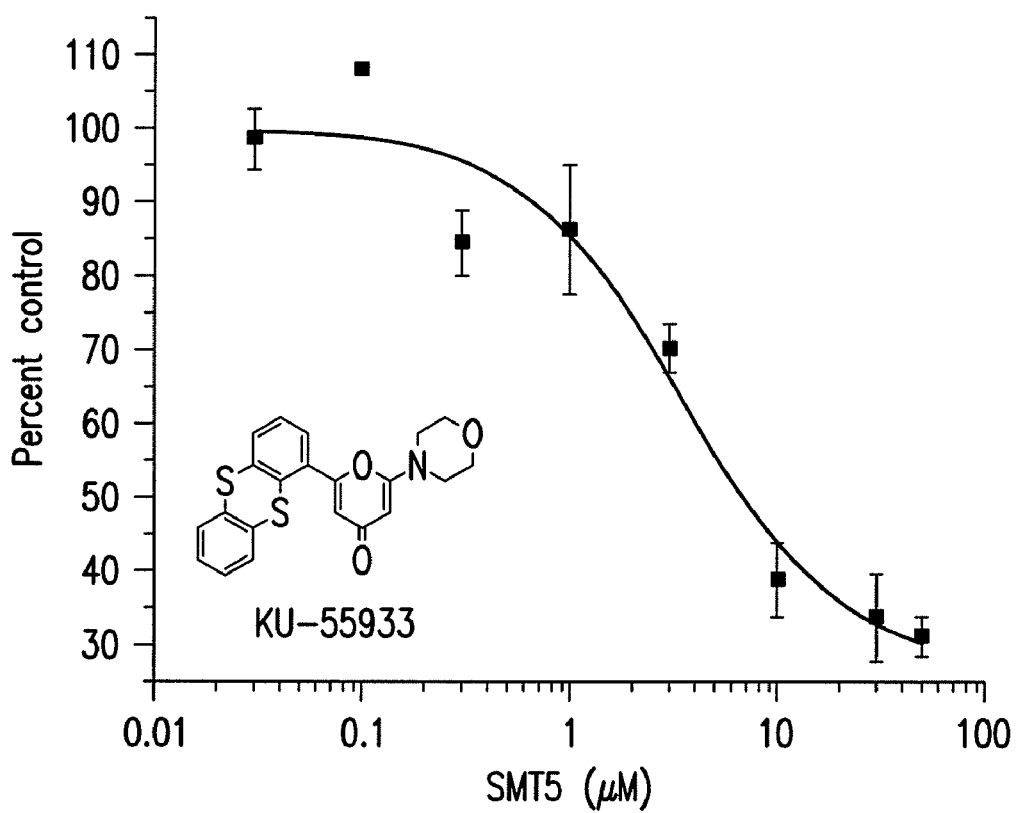

FIG. 18. Change in Aβ42 levels (percent control) in N2a cells stably expressing human APP with the Swedish mutation treated with various concentrations of KU-55933 (SMT5).

Figure 19:
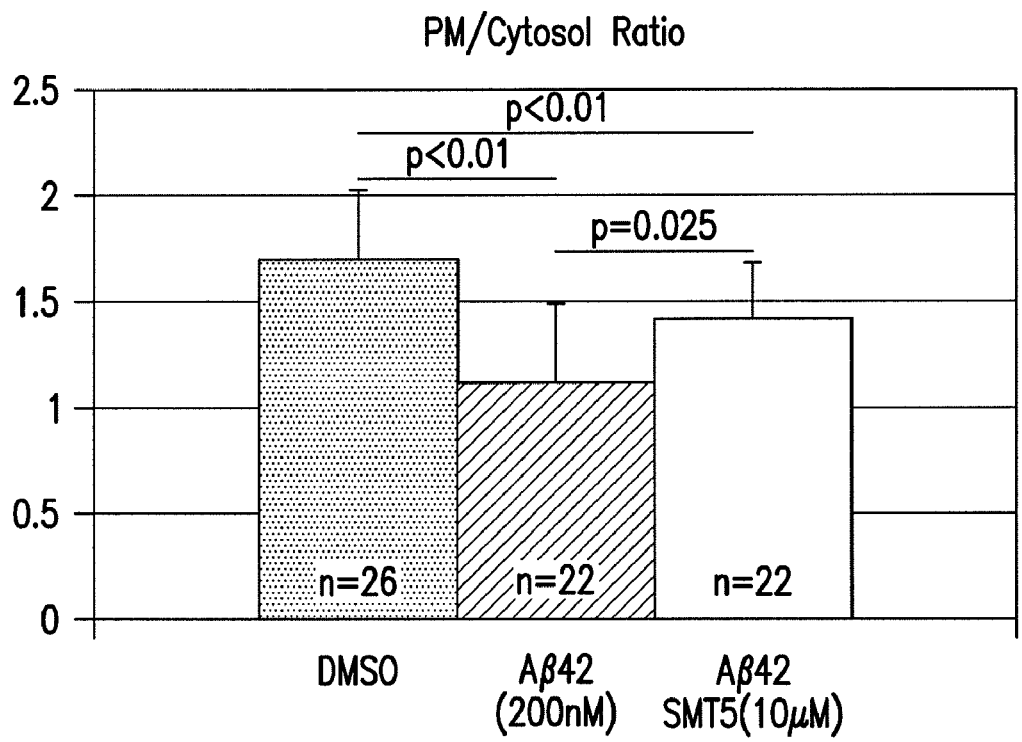

FIG. 19. Plasma membrane/cytosol ratio of PIP2 sensor in PC12 cells treated with Aβ42 with or without KU-55933 (SMT5) relative to DMSO-treated control cells.

Figure 20:
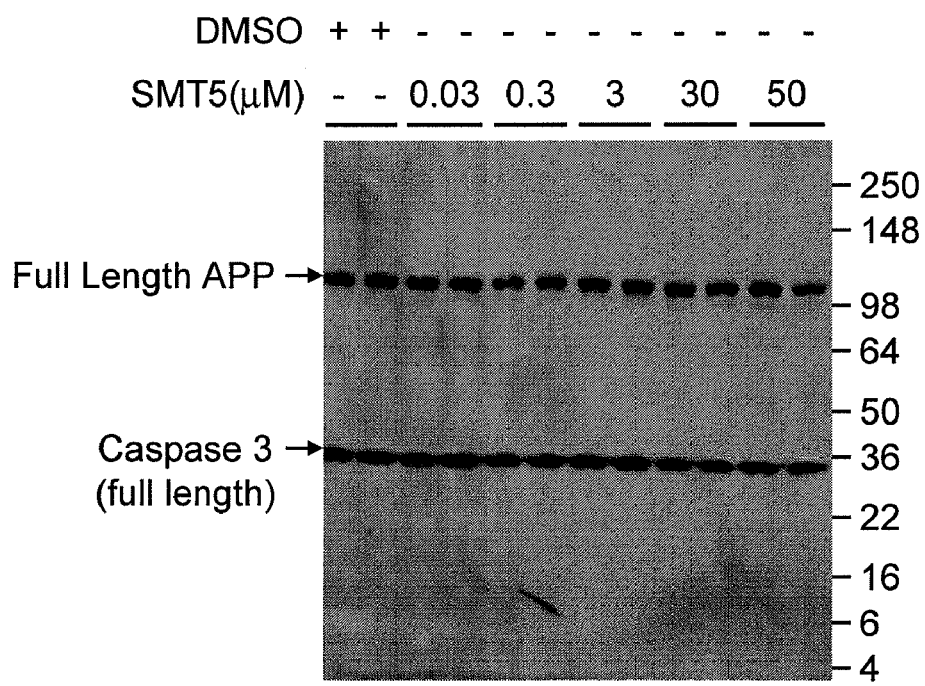

FIG. 20. Western blot showing that caspase 3 remained uncleaved in the presence of increasing concentrations of KU-55933 (SMT5).

Figure 21:
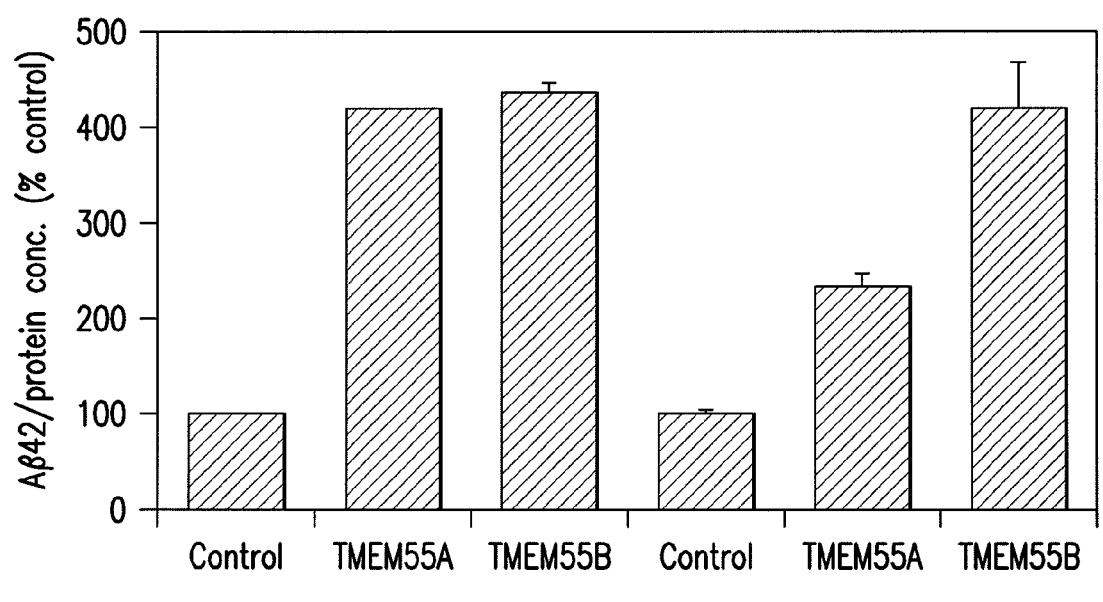

FIG. 21. Overexpression of TMEM55A or TMEM55B leads to the elevated Aβ42 (FIG. 21).

FIG. 22. IC$_{50}$ values for KU-55933 and for various kinases in the PI3 Kinase family as determined by Knight et al. (112).

5. DETAILED DESCRIPTION OF THE INVENTION

For clarity, and not by way of limitation, the detailed description of the invention is divided into the following subsections:
(i) PI4-kinase agonists:
(ii) TMEM55A/B inhibitors;
(iii) PI(4)P5-kinase agonists;
(iv) synaptojanin-1 inhibitors;
(v) PI3-kinase inhibitors;
(vi) ATM Kinase inhibitors;
(vii) agents that decrease PA;
(viii) assay to identify agents that change association of presenilin-1 with lipid rafts;
(ix) agents that change association of presenilin-1 with lipid rafts;
(x) assay to identify agents that increase PIP2 and inhibit Aβ42 toxicity;
(xi) assay to identify inhibitors of synaptojanin-1;
(xii) diagnostic methods;
(xiii) methods of treatment; and
(xiv) other methods.

5.1 PI4-Kinase Agonists

In non-limiting embodiments, the present invention provides for a method of inhibiting the adverse neuronal effects of Aβ42 comprising administering, to a neuron in need of such treatment, an amount of a PI4-Kinase agonist effective in increasing the amount of PIP and/or decreasing the amount of Aβ42 in the neuron.

In further non-limiting embodiments, the present invention provides for a method of treating a neurodegenerative disease in a subject, comprising administering, to the subject, an amount of a PI4-Kinase agonist effective in increasing the amount of PIP and/or decreasing the amount of Aβ42 in a neuron in the subject.

The term "effective amount" as used in this document means an amount determined to have the specified effect on a neuronal cell in an in vitro, ex vivo, or in vivo system. As one non-limiting example, in a culture of neuronal cells exposed to Aβ42 at a concentration which produces a toxic effect (see below), an "effective amount" reduces the magnitude of the toxic effect.

A "toxic effect" of Aβ42, as referred to in this document, includes, but is not limited to, a decrease in PIP, a decrease in PIP2, apoptosis and indicia thereof (e.g., DNA laddering and caspase induction), suppressed CREB phosphorylation, impaired CREB signaling, and inhibition of long term potentiation ("LTP").

In specific, non-limiting embodiments, PI4 kinase agonist is an activator of PI4KIIα, which may be administered to achieve a local concentration in the area of cells to be treated of between about 1 and 200 μM, preferably between about 50 and 150 μM, and preferably between about 80 and 120 μM. In further specific, non-limiting embodiments, the activator of PI4KIIα may be administered, to a human subject containing a cell to be treated, intravenously, subcutaneously, intrathecally, orally, intramuscularly, intranasally, or by other methods.

Applicants have learned that dammarenes, including ginsenosides such as (20S)Rg3, at a concentration that preferably, but not by way of limitation, increases intracellular PIP and/or PIP2 levels, and/or decreases intracellular PA levels, by at least about 10 percent. In this way, such compounds have a positive effect in the treatment of Alzheimer's Disease as well as Mild Cognitive Impairment, as well as other disorders that may be mediated by Aβ42. In specific, non-limiting embodiments, (20S)Rg3 or its derivative may be administered to achieve a local concentration in the area of cells to be treated of between about 1 and 200 μM, preferably between about 50 and 150 μM, and preferably between about 80 and 120 μM. In further specific, non-limiting embodiments, (20S) Rg3 or its derivative may be administered, to a subject containing a cell to be treated, intravenously, subcutaneously, intrathecally, orally, intramuscularly, intranasally, or by other methods known in the art. Administration of (20S)Rg3 has been shown to increase PIP and/or PIP2 levels in neuronal cells treated with Aβ42.

In alternative, non-limiting embodiments, the invention provides for the administration of PI4 kinase agonists excluding dammarenes, such as, but not limited to the ginsenoside (20S)Rg3. For example, certain embodiments of the invention provide for the administration of the non-ginsenoside PI4 kinase agonist, calmodulin-like molecule 17 (122, 123), or a derivative thereof, at a concentration that preferably, but not by way of limitation, increases intracellular PIP and/or PIP2 levels, and/or decreases intracellular PA levels, by at least about 10 percent. Additional non-ginsenoside PI4 kinase agonists that may be administered at such concentrations to achieve such modulation of PIP, PIP2, and/or PA levels include PIK-A49, spermidine, spermine, polylysine, cardiotoxin, melittin, and histone. (128-130). Furthermore, administration of additional PI4 kinase, either via an increase in the expression of the endogenous PI4 kinase gene or via the introduction of one or more additional PI4 kinase gene(s) may also be employed to increase intracellular PIP and/or PIP2 levels, and/or decrease intracellular PA levels. For example, but not by way of limitation, routine gene therapy methods may be employed to introduce additional copies of a sequence encoding PI4 kinase into a cell, e.g., adenovirus- or retrovirus-mediated gene transfer.

5.2 TMEM55A/B Inhibitors

In non-limiting embodiments, the present invention provides for a method of inhibiting the adverse neuronal effects of Aβ42 comprising administering, to a neuron in need of such treatment, an amount of a TMEM55A or TMEM55B inhibitor effective in increasing the amount of PIP and/or decreasing the amount of Aβ42 in the neuron.

In further non-limiting embodiments, the present invention provides for a method of treating a neurodegenerative disease in a subject, comprising administering, to the subject, an amount of a TMEM55A or TMEM55B inhibitor effective in increasing the amount of PIP and/or decreasing the amount of Aβ42 in a neuron in the subject.

Overexpression of TMEM55A or TMEM55B leads to the elevated Aβ42 (FIG. 21). Thus, inhibitors of TMEM55A or TMEM55B may be used to Aβ42 generation. TMEM55A and TMEM55B are phosphoinositide 4-phosphatases, which remove 4-phosphate from either PIP or PIP2. The description for TMEM55A and TMEM55B can be found in the reference (109).

5.3 PI(4)P5-Kinase Agonists

In non-limiting embodiments, the present invention provides for a method of inhibiting the adverse neuronal effects of Aβ42 comprising administering, to a neuron in need of such treatment, an amount of a PI(4)P5 kinase agonist effective in increasing the amount of PIP2 and/or decreasing the amount of Aβ42 in the neuron.

In further non-limiting embodiments, the present invention provides for a method of treating a neurodegenerative disease in a subject, comprising administering, to the subject, an amount of a PI(4)P5 kinase agonist effective in increasing the amount of PIP2 and/or decreasing the amount of Aβ42 in a neuron in the subject.

5.4 Synaptojanin-1 Inhibitors

In further non-limiting embodiments, the present invention provides for a method of treating a neurodegenerative disease in a subject, said disease associated with increased levels of Aβ42, comprising administering, to the subject, an amount of a synaptojanin-1 inhibitor effective in increasing the amount of PIP2 and/or decreasing the amount of Aβ42 in a neuron in the subject.

In one set of embodiments, a Synj1 inhibitor may be an antisense RNA or RNAi that inhibits expression of Synj1. Such molecules may preferably be between 10 and 50 bases (or between 10 and 30 bases) in length and be at least 90 or at least 95 percent homologous to a region of the same size in the Synj1 mRNA or a coding region of the Synj1 gene. In a specific non-limiting examples, such antisense RNA or RNAi may be directed toward the human Synj1 gene having GenBank Acc. Nos. 043426 and NM_203446, or the mouse Synj1 gene having GenBank Acc. Nos. Q62910 and XM_358889, or the rat Synj1 gene, having GenBank Acc. Nos. P50942 and U45479.

In another set of embodiments, a Synj1 inhibitor may be a benzene polyphosphate, for example, but not limited to, biphenyl 2,3',4,5',6-pentakisphosphate, (see, for example, Ref. 115).

5.5 PI3-Kinase Inhibitors

In non-limiting embodiments, the present invention provides for a method of inhibiting the adverse neuronal effects of Aβ42 comprising administering, to a neuron in need of such treatment, an amount of a PI3 kinase inhibitor effective in increasing the amount of PIP2 and/or decreasing the amount of Aβ42 in the neuron.

In further non-limiting embodiments, the present invention provides for a method of treating a neurodegenerative disease in a subject, comprising administering, to the subject, an amount of a PI3 kinase inhibitor effective in increasing the amount of PIP2 and/or decreasing the amount of Aβ42 in a neuron in the subject.

Alpha, beta, and gamma isoform specific or general PI 3-kinase inhibitors may be used (see Refs. 111 and 112). Specific, non-limiting examples of PI3-Kinase inhibitors which may be used according to the invention include those listed in Table I:

TABLE I

| PI3 Kinase Inhibitor | Reference |
| --- | --- |
| PI-103 | WO 01/083456* |
| MPP-IV | Hayakawa et al., (2007), Bioorg. Med. Chem. 15(17): 5837-5844. |
| PIK-75 | WO 01/83481 |
| | Knight et al., (2006), Cell 125(4): 733-747. |
| TGX-221 | Jackson et al., (2005), Nature Med. 11(5): 507-514. |
| TGX-115 | WO 01/53266 |
| | Knight et al., (2004), Bioorg. Med. Chem. 12(17): 4749-4759. |
| IC87114 | WO 01/81346, U.S. Pat. No. 6,518,277 |
| PIK-39 | WO 01/81346, Knight et al., (2006), Cell 125(4): 733-747. |
| AS605240 | Camps et al., (2005), Nature Med. 11(9): 936-943. |
| AS604850 | Camps and Barber, (2005), Nature Med. 11(9): 933-935. |
| AS252424 | Pomel et al., (2006), J Med. Chem. 49(13): 3857-3871. |
| PIK-23 | WO 01/81346 |
| PIK-75 | WO 01/83481 |
| AMA-37 | WO 02/20500 |
| IC60211 | WO 02/20500 |
| IC86621 | WO 02/20500 |
| PIK-93 | WO 03/072557 |
| KU-55933 | WO 03/070726 |
| PIK-124 | WO 04/042373 |
| PIK-90 | WO 04/029055 |
| TGX-286 | WO 04/016607 |
| PIK-108 | WO 04/016607 |

*The numbers prefaced by "WO" herein refer to International Patent Application Publication Numbers.

Additional PI3 Kinase inhibitors which may be used according to the invention are listed in the following published International Patent Applications (Publication Nos.): WO 04/078754; WO 04/007491; WO 04/029055; WO 04/052373; WO 04/056820; WO 04/10878; WO 04/108713; WO 04/108715; WO 04/108716; WO/108709; WO 04/108714; WO 05/023800; WO 05/042519; WO 05/011686; WO 05/068444; WO 04/029055; WO 04/078754; WO 04/096797; WO 05/021519; WO 06/04279; and WO 06/024666.

The $IC_{50}$ values for KU-55933 against various kinases in the PI3 Kinase family are depicted in FIG. 22.

5.6 ATM Kinase Inhibitors

In additional non-limiting embodiments, the present invention provides for a method of inhibiting the adverse neuronal effects of Aβ42 comprising administering, to a neuron in need of such treatment, an amount of a ATM Kinase inhibitor effective in increasing the amount of PIP2 and/or decreasing the amount of Aβ42 in the neuron. The role of ATM Kinase is described in Knight et al., A pharmacological map of the PI3-K family defines a role for p110alpha in insulin signaling. Cell. 2006 May 19; 125(4):733-47.

In further non-limiting embodiments, the present invention provides for a method of treating a neurodegenerative disease in a subject, comprising administering, to the subject, an amount of a ATM kinase inhibitor effective in increasing the amount of PIP2 and/or decreasing the amount of Aβ42 in a neuron in the subject.

A specific, non-limiting example of an ATM Kinase inhibitor which may be used according to the invention is KU-55933. The $IC_{50}$ values for KU-55933 against ATM Kinase are provided in FIG. 22.

5.7 Agents that Decrease Phosphatidic Acid

In non-limiting embodiments, the present invention provides for a method of inhibiting the adverse neuronal effects of Aβ42 comprising administering, to a neuron in need of such treatment, an amount of an agent, that decreases phosphatidic acid (PA), effective in increasing the amount of PIP2 in the neuron.

In further non-limiting embodiments, the present invention provides for a method of treating a neurodegenerative disease in a subject, comprising administering, to the subject, an amount of an agent, that decreases PA, effective in decreasing the amount of PIP2 in a neuron in the subject.

Agents which decrease PA levels include, but are not limited to, an inhibitor of diacylglycerol kinase, an inhibitor of phospholipase D1, and/or an inhibitor of phospholipase D2. [Topham M K. Signaling roles of diacylglycerol kinases. J Cell Biochem. 2006 Feb. 15; 97(3):474-84, and Cazzolli et al., Phospholipid signalling through phospholipase D and phosphatidic acid. Cazzolli R, Shemon A N, Fang M Q, Hughes W E. IUBMB Life. 2006 August; 58(8):457-61.] Preferably, but not by way of limitation, the agent is effective in decreasing PA levels by at least about 10 percent.

Non-limiting examples of agents that may be used to decrease PA include, but are not limited to, siRNA directed toward phospholipase D1 or D2 or diacylgerycerol kinase.

5.8 Assays to Identify Agents that Change Association of Presenilin-1 with Lipid Rafts The present invention provides for methods of identifying agents which alter the association of presenilins with lipid rafts, including but not limited to, presenilin 1 (PS1). Presenilin 1 is a component of the γ-secretase complex, which is responsible for the cleavage of amyloid precursor protein into Aβ42. The γ-secretase complex has been associated with lipid rafts, which are cholesterol-rich regions of the cell membrane which are implicated in the production of Aβ42. Such agents may be utilized to increase or decrease the association of presenilins with the γ-secretase complex, and accordingly alter the activity of the γ-secretase complex with regard to the production of Aβ42.

Preparation of membrane fractions may be performed by any method known in the art. See, for example, Ref. 110. In a preferred embodiment, lipid raft fractions are separated following detergent solubilization using polyoxyethylene(20) oleyl ether (available as BRIJ 98™ from Sigma-Aldrich, St. Louis, Mo.). Cells are washed twice in phosphate-buffered saline and placed into lysis buffer, containing polyoxyethylene(20) oleyl ether (available as BRIJ 98™ from Sigma-Aldrich, St. Louis, Mo.), supplemented with a protease inhibitor tablet (Roche), and lysates incubated at 37° C. Optionally, cells may be homogenized, for example, by passage through a 22 G 1½ needle. Solubilized cell lysate may then be adjusted to contain 40% final concentration of sucrose in ultracentrifuge tube. A discontinuous sucrose gradient may then be formed by the addition of 35% sucrose and 5% sucrose, and centrifuged at 39,000 rpm for 18 hr in SW41 rotor (Beckman Ins.) at 4° C. (fraction 1-top to fraction 12-bottom)

In a non-limiting embodiment, the present invention provides for a method of isolating lipid rafts containing γ-secretase complexes from cell preparations, comprising the steps of:

(1) solubilizing the cell preparations in a solution comprising polyoxyethylene(20) oleyl ether at 37° C. to produce cell lysates;

(2) Adjusting the sucrose concentration of the cell lysates to discontinous sucrose gradient 40% (bottom), 35% (middle), 5% (top) sucrose (final concentration);

(3) Subjecting the cell lysates to ultracentrifugation at 39,000 rpm for 18 h;

(4) Collecting fractions from the top of the gradient; and (5) Identifying fractions containing flotillin;

Wherein the presence of flotillin in a fraction indicates the presence of lipid rafts.

Methods of performing the individual steps of this method will be known to a person of ordinary skill in the art.

Determination of the localization of phosphoinositides, such as presenilin 1, may be performed by any method known in the art. For example, equal volumes of each fraction may be analyzed by Western blotting. Optionally, samples may be concentrated by methanol/chloroform precipitation or subject to immunoprecipitation before analysis.

5.9 Agents that Change Association of Presenilin-1 with Lipid Rafts

In non-limiting embodiments, the present invention provides for a method of inhibiting the adverse neuronal effects of Aβ42 comprising administering, to a neuron in need of such treatment, an amount of an agent that reduces the amount of PS1 in lipid rafts prepared from a cell population expressing PS1.

In further non-limiting embodiments, the present invention provides for a method of treating a neurodegenerative disease in a subject, comprising administering, to the subject, an amount of an agent that reduces the amount of PS1 in lipid rafts.

In one non-limiting example, the agent is (20S)Rg3.

In another non-limiting example, the agent is an agonist of PI4 Kinase.

5.10 Assays to Identify Agents that Increase PIP2 and Inhibit Aβ42 Toxicity

An assay system which utilizes embryonic stem cells differentiated to form neuronal cells and containing a PIP2 sensor is described in PCT/US2006/005745.

In non-limiting embodiments, the present invention further provides for an assay system which utilizes cells, preferably neuronal cells, or cell lines (preferably neuronal cell lines)

engineered to contain a PIP2 sensor. For example, in such assay systems, neuronal cell lines such as but not limited to PC12 cells or N2a cells may be used. Alternatively, non-neuronal cell lines may be used, such as but not limited to CHO. NIH 3t3, HEK293, or HeLa (72).

In a specific, non-limiting embodiment, the pheochromocytoma cell line PC12 may be transfected with a construct encoding a GFP fusion comprising the PH domain of PLCδ1. The PH domain of human PLCδ1 comprises residues 1-170 of the human PLCδ1 amino acid sequence (see e.g., GenBank Acc. No. NP006216 (124)). After 16-24 hrs, epifluorescent microscopy may be used to visualize the distribution of fluorescent GFP-PHPLCδ1 at the plasma membrane as compared to the cytosol. In control cells, the fluorescence should appear as a rim that borders the cells and is thus concentrated at the plasma membrane. Treatment of cells with oAβ42, where oA Aβ42 refers to oligomeric Aβ or any other derivative of Aβ42 or other Aβ species, including Aβ40, should induce, within minutes, a significant disappearance of the probe from the plasma membrane and a corresponding increase of the fluorescence levels in the cytoplasm, which should appear more diffuse. This effect may be mimicked by a treatment with ionomycin, suggesting that it reflects hydrolysis of PtdIns(4, 5)P2 at the plasma membrane. In sensor-transfected cells in the absence of oAβ42, the ability of a test agent to increase PIP2 may be detected as an increase in the ratio of the fluorescence intensity at the plasma membrane to the average fluorescence intensity of the cytosol.

Accordingly, the present invention provides for a method of identifying an agent that increases PIP2 comprising (i) providing a host cell containing a fluorescent GFP-PHPLCδ1 sensor; (ii) administering the test agent to the host cell; and (iii) measuring the ratio of the fluorescence at the plasma membrane to the average fluorescence of the cytosol, where an increase in the ratio indicates an increase in PIP2 levels in the host cell.

In an alternative embodiment, the present invention provides for a method of identifying an agent that inhibits a toxic effect of oAβ42, comprising (i) providing a host cell containing a fluorescent GFP-PHPLCδ1 sensor; (ii) exposing the host cell to a toxic concentration of oAβ42; (iii) administering the test agent to the host cell; and (iv) measuring the fluorescence at the plasma membrane and in the cytosol, where an increase in the ratio of fluorescence in the plasma membrane versus the cytosol indicates that the test agent inhibits a toxic effect of oAβ42.

5.11 Assay to Identify Inhibitors of Synaptojanin-1

The present invention, in a non-limiting embodiment, provides for an assay to identify an inhibitor of Synj1. For example, the assay may comprise (i) recombinant human Synj1 protein (either full-length protein or 5-phosphatase domain); (ii) phosphoinositide (PI) lipid substrate (either PIP2 or brain PI mixture); and (iii) a phosphatase assay known in the art (detecting inorganic phosphate released from phosphatase reaction). For example, full-length human Synj1 having the sequence as set forth in GenBank Acc. NO. NM_203446 may be used, or another molecule comprising its 5-phosphatase domain (residues 513-900 of said sequence) may be used (see Ref. 125).

Several HTS-adaptable phosphatase assays are commercially available, for example, the "PiPer™" assay kit (Invitrogen) (PIPER assay), which allows for quantitative measurement of free phosphate groups generated from the phosphatase assay. Alternatively, a 5-phosphatase assay based on fluorescence polarization may be used (e.g., the 5-phosphatase assay kit sold by Echelon or the Phosphate Sensor assay kit sold by Invitrogen).

For the Synj1 activity assay, recombinant Synj1 protein and lipid substrates (e.g. PIP2) may be introduced into multi-well assay plates, together with a test compound, and then one of the above-mentioned phosphatase assays may be performed. Using multi-well assay plates permits for high throughput screening.

In addition, assays such as those used to identify inhibitors of SHIP2 may be modified to identify inhibitors of Synj1 by replacing SHIP2 with Synj1 or its 5-phosphatase domain. See, for examples, Refs. 116-121.

Because desirably an inhibitor for use according to the invention shows selective inhibitory activity toward Synj1, but not other members of the inositol 5'-phosphatase family, in specific embodiments of the invention, the assay further comprises a counter-screening step against another member of the family, for example, but not limited to, SHIP2. The counter-screening step may comprise (i) recombinant inositol-5 phosphatase which is not Synj1 (e.g., SHIP2, Synj2, INPP5P, OCRL, SHIP1, SKIP, PIPP, Pharbin/INPP5E, PTEN, MINPPI, INPPI5, Sac1, Sac2, or Sac3) (ii) phosphoinositide (PI) lipid substrate (either PIP2 or brain PI mixture); and (iii) a phosphatase assay (detecting inorganic phosphate released from phosphatase reaction). Accordingly, in a specific non-limiting embodiment of the invention, the present invention provides for a method of identifying an agent useful in treating neurodegeneration and/or protecting a neuron from the toxic effects of oAβ42, comprising identifying, as set forth above, a compound which selectively inhibits Synj1 relative to another inositol 5-phosphatase, such as SHIP2, Synj2, INPP5P, OCRL, SHIP1, SKIP, PIPP, Pharbin/INPP5E, PTEN, MINPPI, INPPI5, Sac1, Sac2, or Sac3.

5.12 Diagnostic Methods

The present invention also provides for methods of diagnosing a neuro-degenerative disorder, for example, a neuro-degenerative associated with increased levels of Aβ42, comprising measuring the level of phosphoinositide metabolism in a subject. The measurements may be derived from samples taken from the brain, or may be derived from samples taken from the periphery, e.g., peripheral blood samples. In a particular, non-limiting example, the method comprises measuring the level of activity of compounds and molecules associated with the generation and/or breakdown of phosphatidic acid (PA) in a subject, wherein a change in the level of activity of compounds and molecules associated with the generation and/or breakdown of phosphatidic acid (PA) in a subject, relative to the level of activity in a normal, healthy sample, indicates that the subject suffers from a neurodegenerative disease.

The diagnosis of a neurodegenerative disorder, such as Alzheimer's Disease, will vary based upon the particular phosphoinositide molecule under study, and the source of the test sample. For example, the level of activity may decrease for a particular phosphoinositide molecule under study with regard to a sample derived from the brain, but may increase with regard a sample derived from the periphery. In a non-limiting example, a decrease in the level of activity, in the brain, of phosphoinositide metabolism in compounds or molecules associated with the generation and/or breakdown of phosphatidic acid (PA) indicates a diagnosis of Alzheimer's Disease (AD). In another non-limiting example, an increase in the level of activity, in the brain, of phosphoinositide metabolism in compounds or molecules associated with the generation and/or breakdown of PIP2 indicates a diagnosis of Alzheimer's Disease (AD).

Monitoring the relative levels of PA, PI, PI(4)P, PI(4,5)P2 in the AD samples, such as cerebro-spinal fluids (CSF), serum, or plasma, as compared to those found in control samples. Control sample values are defined as values associated with normal patients who do not exhibit evidence of neurdegenerative disease, such as Alzheimer's or Parkinson's disease. In addition, detecting the levels of these lipids in biological fluids, such as plasma, can also be used to monitor the efficacy of the phosphoinositide-modulating drug(s) in animals and humans.

The measurement of phosphoinositide metabolism may be achieved by any method known in the art. In a non-limiting embodiment, the measurement of phosphoinositide metabolism may be performed by HPLC lipid analysis, mass spectrometry, ELISA (using antibody that selectively bind to PIP2 or other specific lipid), lipid kinase assay, and/or thin layer chromatography. An example of these techniques is provided in more detail below.

5.13 Methods of Treatment

The present invention provides for pharmaceutical compositions comprising effective amounts of the foregoing agents/compounds, separately or in combination, in a suitable pharmaceutical carrier. The foregoing agents/compounds may be administered orally, intravenously, subcutaneously, intramuscularly, intranasally, intrathecally, or by other methods, several of which are known in the art, as would be appropriate for the chemical properties of the compound. It will be apparent to a person of ordinary skill in the art to determine the appropriate method of delivery of the foregoing agents/compounds.

Neurodegenerative conditions which may be treated according to the present invention include, but are not limited to, mild cognitive impairment, Alzheimer's disease, Pick's disease, Parkinson's Disease, Huntington's Disease, and prion-associated diseases.

The term "treating" as used herein, means that one or more of the following are achieved: (i) a slowing of disease progression; (ii) an increase in survival; (iii) an increase in quality of life; and/or (iv) improved performance on a test of cognition.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

5.14 Other Methods

In additional embodiments, the present invention provides for a method of marketing a drug, as disclosed herein, for the prevention or treatment of AD, comprising a system for disseminating information which includes a direct or indirect representation that the drug increases PIP2 in at least a subset of neurons, where an indirect representation includes statements that the drug is one or more of the following: an agonist of PI4-kinase, an inhibitor of TMEM55A/B, an agonist of PI(4)P5-kinase, an inhibitor of synaptojanin 1, an inhibitor of PI3-kinase, an agent that decreases levels of PA, and/or an agent that reduces the amount of presenilin-1 C-terminal fragment associated with a lipid raft. For example, and not by way of limitation, such system for dissemination of information can occur via electronic means, e.g. via a network of computers, or other automated means. In addition, such system can make use of electronic means for storing and indexing historical data relating to such dissemination as well as measuring the effectiveness of such dissemination and forecasting means for optimizing the efficiency of such dissemination. In addition, such marketing of the drug may be directed towards, retail sales direct consumers, sales to prescribers such as medical doctors, to health maintenance organizations or any other person or entity related to the decision of purchasing the drug or reimbursing of costs associated with that drug, including healthcare providers, which are defined as persons or institutions that directly or indirectly provide healthcare to persons, e.g., hospitals, clinics, formulary managers, insurance carriers, etc. Such marketing also includes marketing to potential investors, such as, but not limited to, marketing for financing to fund a company involved in commercializing the drug.

The following working examples are provided to illustrate various aspects of the invention, and the disclosure of methods and compositions in the following examples are hereby incorporated by reference into the Detailed Description of the Invention.

6. EXAMPLE

Effect of Amyloid Beta-42 on Phosphoinositides—Part I

HPLC Lipid Analysis. Cells grown in 15-cm² dishes were scraped in 0.75 ml ice-cold MeOH: 1M HCl (1:1) supplemented with 2 mM $AlCl_3$. Lipids were then extracted and deacylated by incubation with 0.5 ml methylamine reagent (MeOH:40% methylamine in water:n-butanol:water 47:36:9:8) at 50° C. for 45 min. The aqueous phase was dried, resuspended in 0.5 ml of n-butanol: petroleum ether:ethyl formate (20:40:1), and extracted twice with an equal volume of water. Aqueous extracts were dried, resuspended in water, and subjected to anion-exchange HPLC on an Tonpac AS11-HC column (Dionex). Negatively charged glycerol head groups were eluted with a 1.5-86 mM KOH gradient and detected online by suppressed conductivity 75 in a Dionex Ion Chromatography system equipped with an ASRS-ultra II self-regenerating suppressor. Individual peaks were identified and peak areas were calculated using the Chromeleon software (Dionex). Using deacylated anionic phospholipids as standards, lipid masses were calculated and expressed as molar fractions of total anionic phospholipids present in the sample (see Ref. 69).

Lipid kinase assay and thin layer chromatography. In vitro lipid phosphorylation assays on post-nuclear supernatant of HEK293, Neuro2a or CHO cells expressing either WT or FAD mutant PS1 and PS2, were carried out as previously described (70). In vitro lipid phosphorylation assays on post-nuclear supernatant of HEK293, Neuro2a or CHO cells expressing either WT or FAD mutant PS1 and PS2, were carried out. Briefly, 100 µg protein from the supernatant were mixed with 2.5 µl ATP (final: 50 µM), 2.5 µl CaCl2 (final: 50 µM), 27.0 µl EGTA-free kinase buffer (25 mM Hepes, 100 mM KCl, 2.5 mM MgCl2) and 0.5 µl gamma ATP (final 100 nCi/µl) and samples incubated at 37° C. for 15 min. Reaction products were extracted and analyzed by thin layer chromatography (TLC) silica plate (solvent: 64—acetone 30—methanol 24—acetic acid 32—water 14 (v/v)) and visualized by autoradiography.

Treatment of cultured neurons with aβ42. Treatment of cultured neurons with oligomeric forms of Aβ42 leads to reduced PIP2 levels and increases in the levels of PA. 2-week-old, cultured mouse cortical neurons were incubated with three different Aβ42 preparations (monomers, soluble oligomers, and fibrils) at concentrations of 200 nM. See FIG. 2. The levels of PIP2 were measured by conductance-based HPLC quantitation. Soluble Aβ42 oligomers led to selective decreases in the levels of PIP2 while other lipid species, such as PI or PIP, were not affected. PA levels were up-regulated by the oligomers as well as other Aβ42 species, including monomers and fibrils. PhosphatidylSerine (PS) was also affected by all three preparations. See FIGS. 2A-B. FIG. 2C depicts a time-course of PIP2 reduction and PA increase resulting from exposure of the cultured neurons with Aβ42 oligomers, showing the percent increase or decrease relative to the baseline (time zero) value over a period of 72 hours. The reduction in PIP2 levels and corresponding increase in PA levels were observed within 10 min of the treatment with the Aβ42 oligomers and peaked at 2 hrs. PIP levels were not affected under these conditions.

FIG. 3A-B shows the effect of Aβ42 on the lipid profile of neurons derived from ES cells. FIG. 3A shows that no differences were observed in lipid profiles of cortical neurons from wild-type mice compared with neurons derived from ES cells. FIG. 3B shows that oligomeric Aβ42 was found to also lower PIP2 levels in ES-derived neurons.

7. EXAMPLE

Effect of Amyloid Beta-42 on Phosphoinositides—Part II

To test whether soluble oligomers of Aβ42 affect PIP2 metabolism in neurons, primary cultures were prepared from mouse neonatal cortices, allowed to differentiate for 15 days and incubated with a crude oligomer preparation made from synthetic Aβ42 peptides (oAβ42). This preparation contains a mixture of monomers, trimers and tetramers as well as traces of dimers and high molecular weight oligomers, as described previously. Potential effects of this preparation were investigated either after an acute (0-120 min) or a subchronic treatment (72 h). The levels of phosphoinositides as well as a variety of other anionic phospholipids were measured and quantified in neuronal extracts using HPLC combined with suppressed conductivity detection (69, 71).

Figure 4A:
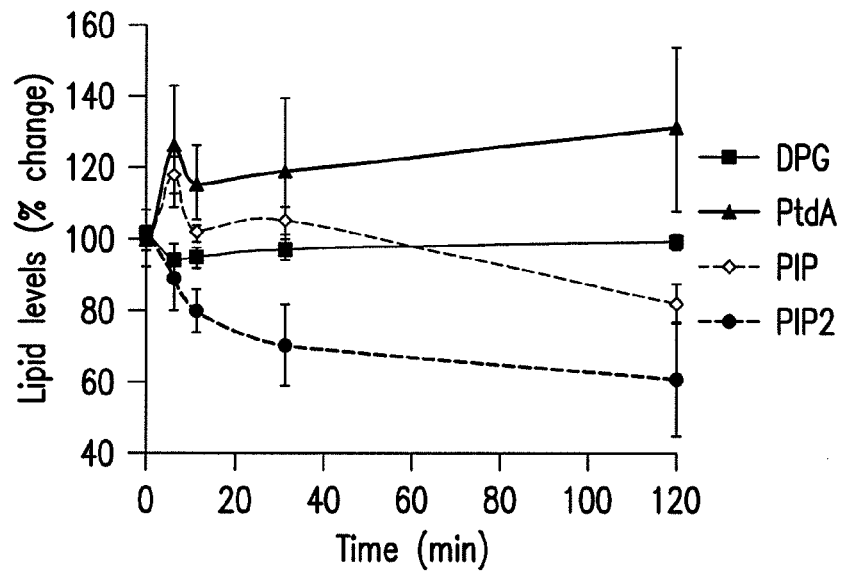

As shown in FIG. 4A, Aβ42 oligomers induced a rapid and progressive decrease in the levels of PIP2 that appear to stabilize at approximately 60% of control (vehicle) levels after 120 min. No significant changes were observed in the levels of most other lipids, although a trend for a transient increase in PIP was seen after 5 min. Additionally, PtdA showed an initial peak after 5 min and a more sustained increase after 30 min to reach approximately 130% of control levels after 120 min, although with a higher variability compared to all other lipids. No effect on PIP2 or other lipids was observed using a control peptide that contains the inverse sequence (Aβ42Rev) or with a preparation of the shorter and non-cytotoxic Aβ peptide, Aβ38, which was processed similarly to oAβ42 (FIG. 4B).

Figure 4B:
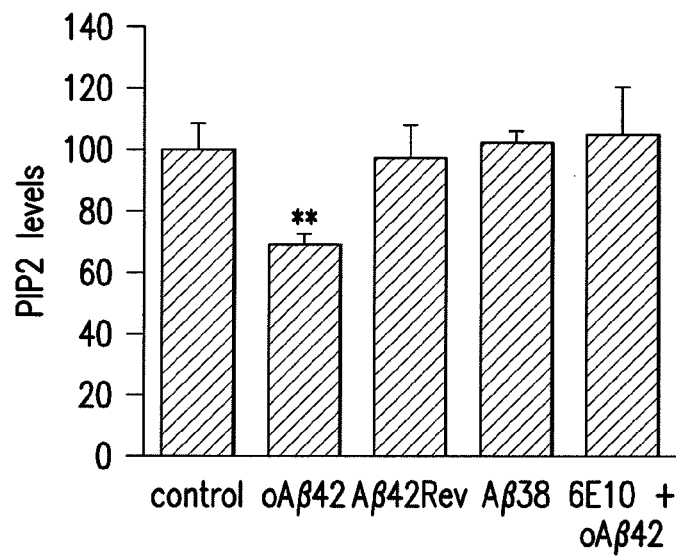

Additionally, Aβ-induced PIP2 deficiency was rescued by preincubating the crude oligomer preparation with antibody 6E10, which is directed to the first 17 amino acids of the NH2-terminus of Aβ42 (FIG. 4B). Soluble oligomers of Aβ42 also produced a decrease in the levels of PIP2 after a 3-day treatment, suggesting that the effects of oligomers on this lipid are long-lasting.

Figure 4C:
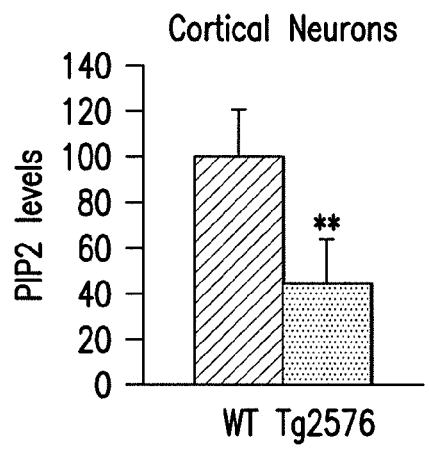
Figure 4D:
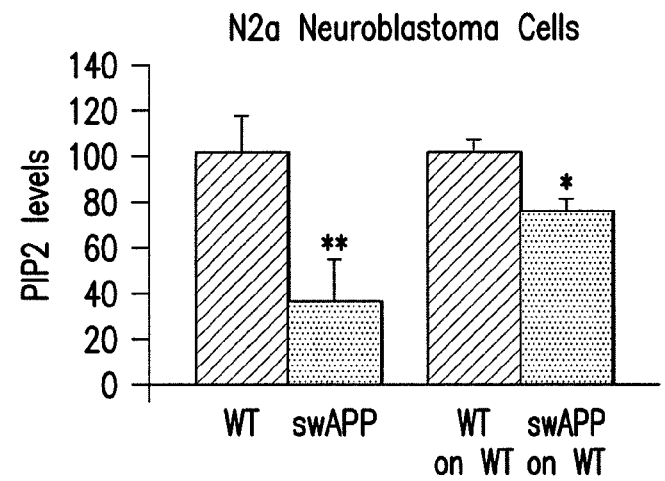

PIP2 dyshomeostasis also occurs in neurons/neuroblastoma expressing APPsw. To rule out potential artifacts inherent to the use of synthetic peptides, experiments were performed to determine whether Aβ produced naturally from cells expressing the "Swedish" mutant of APP (swAPP) also affected PIP2 levels. Primary neurons were prepared from the cortex of transgenic mice expressing swAPP [Tg(swAPP)] under the control of the PrP promoter. After two weeks in culture, Tg(swAPP) neurons exhibited a 58% decrease in the levels of PIP2 compared to neurons prepared from their control littermates (FIG. 4C). This biochemical deficiency was also observed in the N2a neuroblastoma cell line expressing the same mutant (FIG. 4D). Additionally, conditioned medium from N2a swAPP-expressing cells (diluted 1:4) induced a decrease in the levels of PtdIns(4,5)P2 after a 3-day treatment in control neuroblastoma suggesting that secreted Aβ mediates the observed effect on the metabolism of PIP2.

Figure 4E:
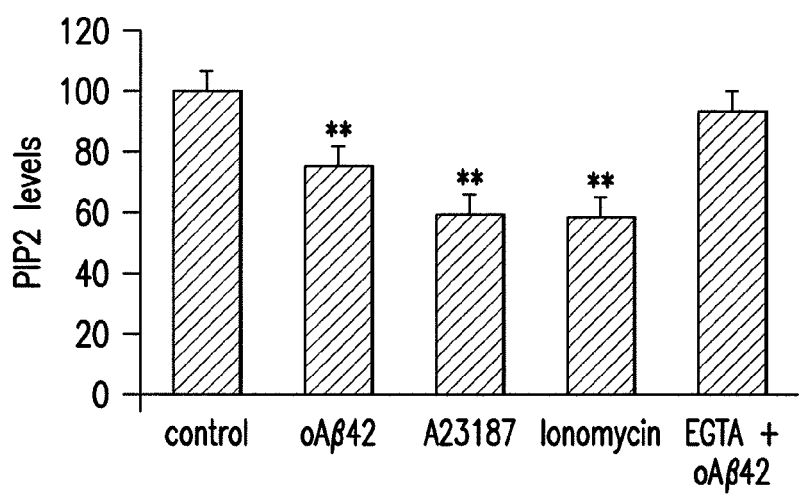

Growing evidence suggests that soluble oligomers of Aβ42 trigger Ca2+ dyshomeostasis. Experiments were performed to determine whether Aβ42-induced PIP2 deficiency is mediated by extracellular Ca2+; the results are shown in FIG. 4E. Cortical neurons were treated with oAβ42 for 60 min in the presence or absence of the cell-impermeable Ca2+ chelator EGTA (2 mM). Results show that chelation of extracellular Ca2+ prevented oAβ42 from decreasing PIP2 levels. Cell-permeable Ca2+ chelator BAPTA-AM also blocked the action of oAβ42, although sequestration of both extracellular and intracellular Ca2+ led to a 2-fold increase in the levels of PtdIns(4,5)P2 in both vehicle-treated and oAβ42-treated cortical neurons. In parallel experiments, a treatment of neurons with the Ca2+ ionophores ionomycin and A23187 (2 μM) caused PIP2 levels to decrease, although the latter effects were more dramatic compared to that of oAβ42. Together, these experiments suggest that the basis for Aβ42-induced PIP2 deficiency is calcium dyshomeostasis.

Aβ-induced PIP2 deficiency is not simply the result of cell death because the amount of pyknosis occurring after a 3-day treatment with oAβ42 was undistinguishable from that occurring in vehicle-treated neurons (FIG. 5A) and the number of apoptotic nucleic were comparable or slightly less in oAβ42-treated neurons (FIG. 5B). Furthermore, PIP2 deficiency does not reflect a breakdown in energy balance, based on our findings that ATP levels are normal after oAβ42 treatment at the concentration used (200 nM) (FIG. 5C). These results are in agreement with independent studies showing that Aβ does not induce cell death unless used in the micromolar range.

8. EXAMPLE

Effect of Synj1 Levels On PIP2 and oAβ42 Toxicity

To study the effects of modulation of Synj1, mice having a "knock-out" of Synj1 were prepared. While mice homozygous for the knock-out mutation died perinatally, Synj1 heterozygotes (Synj1$^{+/-}$) have no discernable phenotype and are thus indistinguishable from wild type animals. FIG. 6 shows the results of experiments measuring the fast excitatory postsynaptic potential (V/s) in response to an electrical stimulus, and demonstrates that Synj1$^{+/-}$ mice were found to exhibit normal basic synaptic transmission despite having less Synj1. This indicates that reduced Synj1 gives rise to the desired phenotype in the absence of apparent cell abnormalities and reduced Synj1 activity may still be sufficient for carrying out normal brain function.

Experiments were performed to evaluate the effect of less Synj1 in the Synj1$^{+/-}$ mice on PIP2 levels. As shown in FIG. 7, analysis of whole brain lipids from the mouse mutants indicates that levels of PIP2 vary as a function of the number of copies of Synj1. Overexpression of Synj1 (as in the Down Syndrome gentic mouse model Tg(Synj1)) leads to decreased levels of PIP2 in the adult mouse brain, while the brain of a partial knockout mice for Synj1 (Synj1$^{+/-}$)) contains higher levels of PIP2.

The effect of oAβ42 on PIP2 levels and long-term potentiation ("LTP") in mice with genetically modified Synj1 levels was also tested. Synj1$^{+/-}$ mice were used in experiments addressing the effects of oAβ42 on synaptic plasticity in adult hippocampal slices. As shown in FIG. 8A, Synj1$^{+/-}$ mice show a 50% decrease in the levels of Synj1 in whole brain tissue. HPLC measurements of PIP2 levels in whole brain and in 15 DIV cortical cultures showed a 10% and a 20% increase in Synj1$^{+/-}$ relative to control tissue/cells, respectively (FIG. 8B). Long-term potentiation (LTP) was induced in the CA1 region of the hippocampus through tetanic stimulation of the Schaeffer collateral pathway. Potentiation in Synj1$^{+/+}$ slices was comparable to that obtained in Synj1$^{+/-}$ slices in the presence of vehicle (FIG. 8C). However, while oAβ42 partially impaired LTP in control slices, as reported before, the crude oligomer preparation did not affect LTP in Synj1$^{+/-}$ slices. This result indicates that lower levels of synaptojanin 1 and thus higher levels of PIP2 exert a protective effect against soluble oligomers of Aβ.

9. EXAMPLE

Assay System for PIP2 Modulators

Cell culture. PC12 cells were maintained in Dulbecco's modified Eagle's medium with sodium pyruvate (Invitrogen) supplemented with 5 percent fetal bovine serum, 10 percent horse serum, glutamine (4 mM), penicillin (200 units/ml), streptomycin (200 μg/ml); N2a cells were maintained in Dulbecco's modified Eagle's medium supplemented with 10 percent fetal bovine serum, and glutamine, penicillin, and streptomycin as described above. Cells were maintained at 37° C. in 5 percent $CO_2$. Twenty-four hours before transfection, PC12 cells were plated (at 50 percent confluence) on coverslips pre-coated with polylysine (20 μg/ml) for 1 hr at 37° C. Transfections of GFP fusion of the PH domain of human phospholipase Cδ1 (amino acids Met1-Ile 175) ("GFP-PH-$_{PLC\delta1}$") were obtained using Lipofectamine 2000 (Invitrogen). Primary cultures from cortical neurons were generated from newborn mice as described (126). Briefly, cortices were dissected out, trypsinized for 45 minutes, and then dissociated with a Pasteur pipette and plated on poly-ornithine coated 10 mm dishes at a density of 25,000 cells/cm$^2$ in Neurobasal-A medium containing 1 mM kyneurenic acid to reduce enhanced synaptic transmission due to the high density of the cultures. Treatments with Aβ42 were typically performed after 15 DIV, and incubation time with oAβ42 was 60 minutes unless otherwise specified. Drugs were added to the cultures 30 minutes before the addition of oAβ42.

Peptide Preparation.

Solubilization of Aβ3 peptide. Synthetic Aβ (1-42) peptide was purchased from American Peptide (Sunnyvale, Calif.) and stored at −20° C. The peptide containing vial was allowed to equilibrate to room temperature for at least 30 minutes before resuspension. In a fume hood the peptide was diluted to 1 mM in 1,1,1,3,3,3-Hexafluoro-2-propanol (HFIP) by pipette mixing and immediately aliquoted in polypropylene microcentrifuge tubes. The solution was vortexed briefly, and allowed to evaporate in the fume hood for 2 hours. The resulting peptide films were dried in a Speed Vac for 10 minutes at 800 g and stored at −20° C. Prior to use the peptide film was resuspended to 1 mM in dimethyl sulfoxide (DMSO) by pipette mixing followed by bath sonication for 10 minutes. The solution was aliquoted in polypropylene microcentrifuge tubes and stored at −20° C. The peptide was used within two weeks of dilution in DMSO.

Oligomeric forming conditions. The 1 mM DMSO solution was diluted to 100 μM in cold phosphate buffered saline (PBS), vortexed for 30 seconds, and incubated overnight at 4° C. (minimum incubation of 12 hours). Immediately before use the Aβ-PBS solution was further diluted in culture media to the required final concentration and vortexed briefly.

Monomeric conditions. Following bath sonication the 1 mM DMSO solution was immediately diluted in culture media to the final concentration.

Fibril forming conditions. The 1 mM DMSO solution was diluted to 100 μM in 10 mM HCl, vortexed for 30 seconds and incubated overnight at 37° C. (minimum incubation of 12 hours). Immediately before use the solution was diluted in culture media to the required final concentration and vortexed briefly.

Lipid measurements. Cultures were scrapped on a methanol:1N HCl 1:1 buffer supplemented with 2 mM $AlCl_3$. Ice-cold chloroform (0.4 ml) was then added, and samples were vortexed for 1 min. The solvent phase was washed with 1 ml. methanol:2 mM oxalic acid (1:0.9 vol/vol) and dried under a flow of nitrogen. Lipids were then deacylated by incubation with 0.5 ml methylamine reagent (MeOH: 40 percent methylamine in water:n-butanol:water 47:36:9.8) at 50° C. for 45 min. The reaction products were dried in a Speed-Vac, resuspended in 0.5 ml n-butanol:petroleum ether:ethyl formate (20:40:1) and extracted twice with an equal volume of water. Extracts were dried in a Speed-Vac, resuspended in water, and subjected to anion-exchange HPLC on an Ionpac AS11-HC column (Dionex). Negatively charged glycerol head groups were eluted with 1.5-86 mM KOH gradient and detected online by suppressed conductivity in a Dionex Ion Chromatography system equipped with an ASRS-ultra II self-regenerating suppressor. Individual peaks were identified and quantified by injection of individual standards. The area under the peaks was used to calculate the molar fraction of each anionic phospholipid present in the extracts. In the case of whole brain analysis, animals were sacrificed and brains were quickly removed and frozen in liquid nitrogen prior to storage at −80° C. Frozen tissue was homogenized using a Teflon pestle in a glass tube in 10 volumes ice-cold chloroform:methanol:10N HCl 20:40:1 supplemented with 2 mM $AlCl_3$. After transferring the samples to Eppendorf tubes, 300 μl chloroform and 500 μl water were added and the extracts were vigorously vortexed for 1 min followed by a 2 min centrifugation step at maximal speed in a microfuge for phase separation. From this point, sample preparation was then continued in a similar manner to that of the cellular cultures. See Ref. 127.

Confocal microscopy. After 24 hours of transfection with GFP-PH$_{PLC\delta1}$, PC12 cells were incubated with 200 μM oAβ42, 2 μM ionomycin (Sigma Aldrich), Aβ42Rev (inverted peptide), or 200 μM Aβ38 oligomers. Cells have been analyzed after being treated for different time lengths: 0, 10 minutes, 30 minutes and 120 minutes. Cells were washed in phosphate buffer and fixed with 4 percent paraformaldehyde. Confocal z-stack images (0.5 μm) of PC12 cells were obtained using Nikon EZ-C1.2.30 confocal microscope, (×100) oil immersion objective. Quantification of GFP intensity was calculated using the ImageJ software: for each cell in a given image, a line intensity profile across the cell was obtained. The relative decrease in plasma membrane localization was calculated as the ratio between the plasma membrane fluorescence intensity and the average cytosolic fluorescence intensity. The average of the ratio was reported in the graph.

Figure 9D:
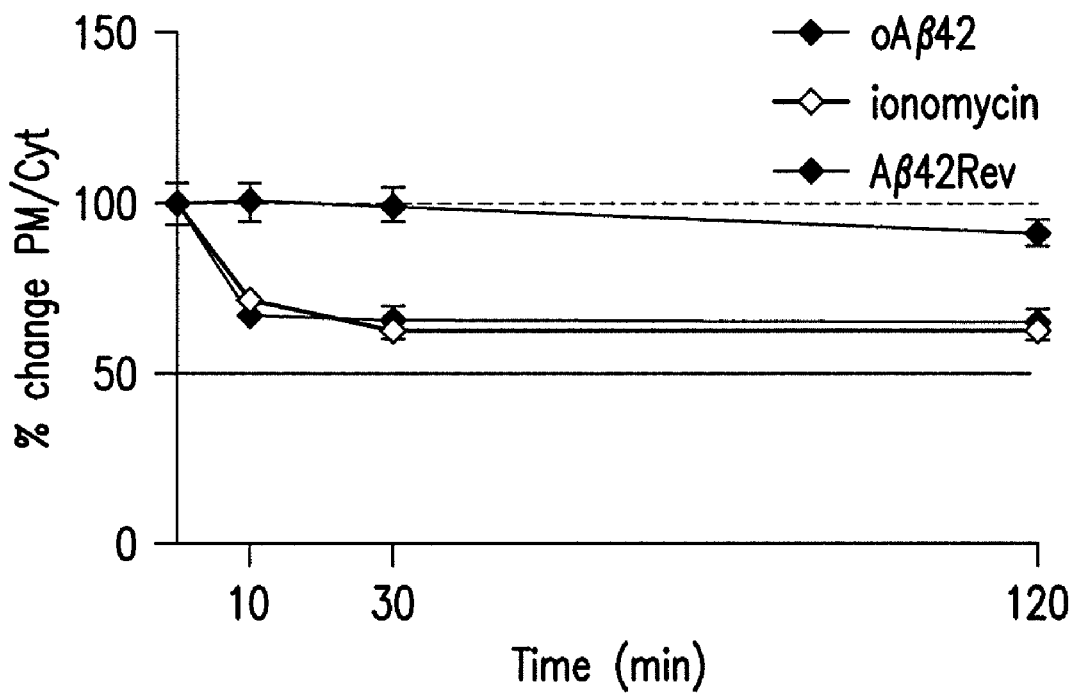
Figure 9E:
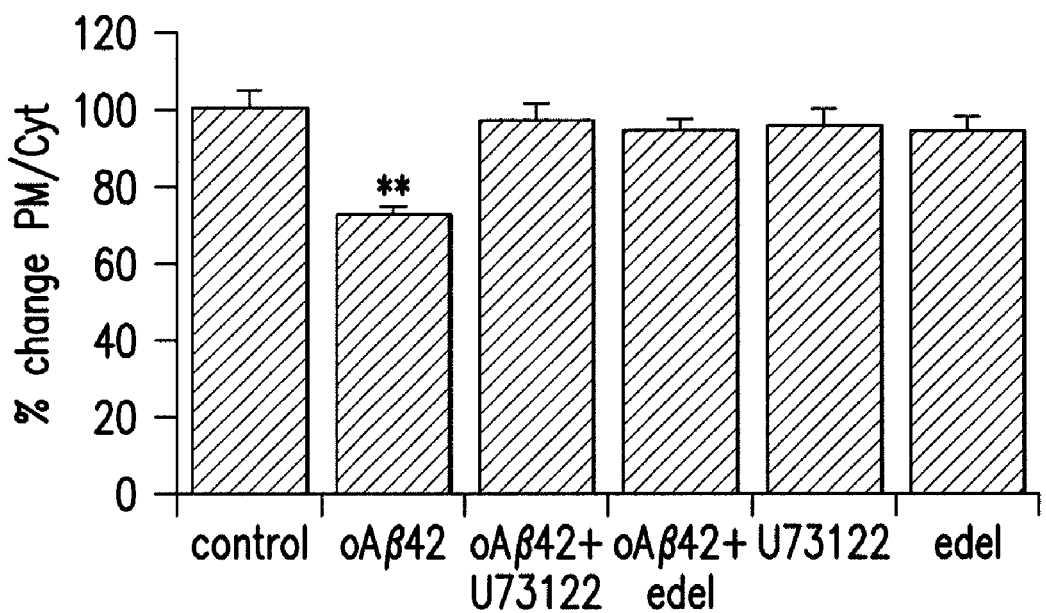

Results. The pheochromocytoma cell line PC 12 was transfected with a construct encoding a GFP fusion of the PH domain of PLCδ1. After 16-24 hrs, visualization of transfected PC12 cells with epifluorescence microscopy revealed that the fluorescence of GFP-PHPLCδ1 appeared as a rim that borders the cells and is thus concentrated at the plasma membrane (FIG. 9A). Treatment of cells with oAβ42 induced within minutes a significant disappearance of the probe from the plasma membrane and a corresponding increase of the fluorescence levels in the cytoplasm, which appeared more diffuse (FIG. 9B). This effect was mimicked by a treatment with ionomycin (FIG. 9C), suggesting that it reflects hydrolysis of PIP2 at the plasma membrane. No significant change in the probe localization was observed when cells were exposed to Aβ42Rev (FIG. 9D).

A major pathway activated by elevated intracellular calcium is that of phospholipase C (PLC), which consists of a family of lipid enzymes that hydrolyzes PIP2 to diacylglycerol (DAG) and inositol-1,4,5-trisphosphate [Ins(1,4,5)P3]. Thus, oAβ42-induced PIP2 deficiency may be caused by an activation of PLCs. To test this hypothesis, PC12 cells were treated with oAβ42 for 60 min in the presence or absence of the PLC inhibitors U73122 or edelfosine (0.5 µM). Results show that PIP2 levels remained unaffected by oAβ42 in the presence of these compounds (FIG. 9E), suggesting that oAβ42 decreases the levels of PIP2, at least in part, by promoting its hydrolysis through the PLC pathway.

10. EXAMPLE

(20S)Rg3 Increases PIP2 by Modulating PI4KIIα

(20S)Rg3 (FIG. 10A) can promote PIP2 synthesis and inhibit Aβ42 generation. Treatment of neurons with 100 µM (20S)Rg3 leads to the increased steady-state levels of both PIP and PIP2 (FIG. 10B) Since (20S)Rg3 modulates both PIP and PIP2, it was hypothesized that the compound may modulate the activity of a kinase (e.g. PI 4-kinase) that mediates the formation of PIP, the rate-limiting precursor for PIP2.

The following experiments were performed to test this hypothesis.

Figure 10A:
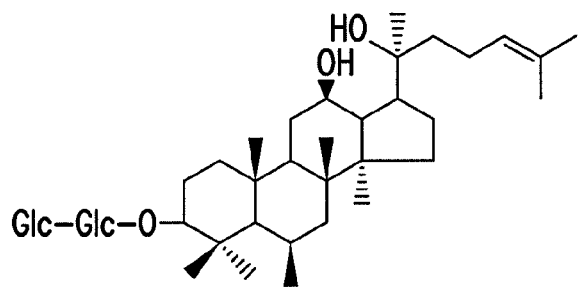
Figure 10B:
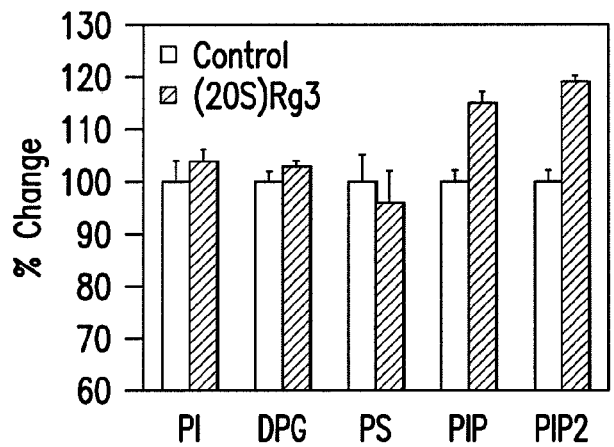
Figure 10C:
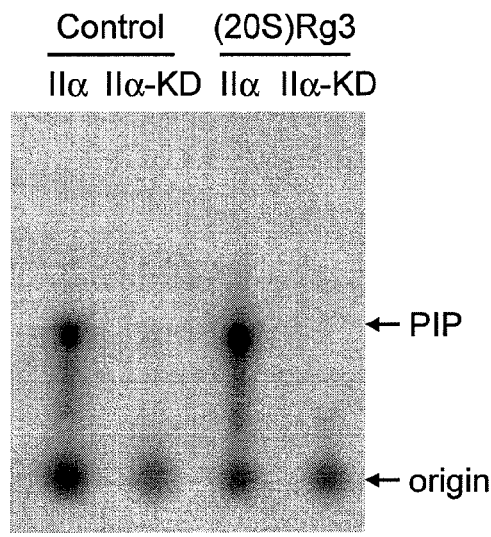
Figure 10D:
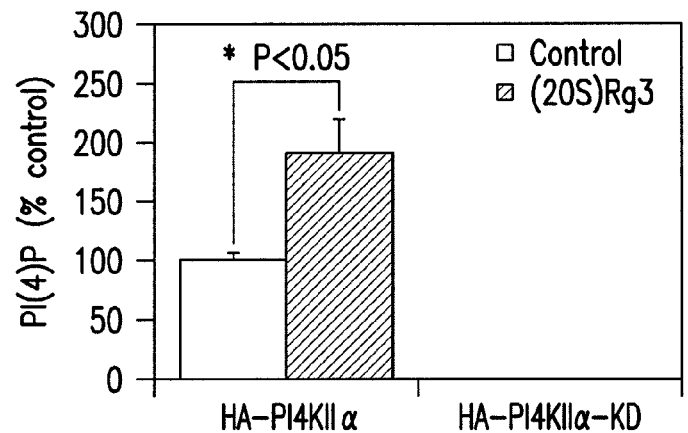

Mammalian expression of a construct encoding either wild-type (IIα) or the kinase-dead mutant (IIα-KD) forms of PI4KIIα (HA-tagged) were transfected into CHO cells. The enzyme was immuno-isolated using anti-HA affinity beads from cell extracts. The purified PI4KIIα proteins were subjected to a lipid kinase activity assay and TLC analysis using PI as a substrate (FIG. 10C). PI4KIIα, but not the kinase-dead mutant, enhanced the incorporation of [γ32P]-ATP into PIP (FIG. 10C,D).

Figure 10E:
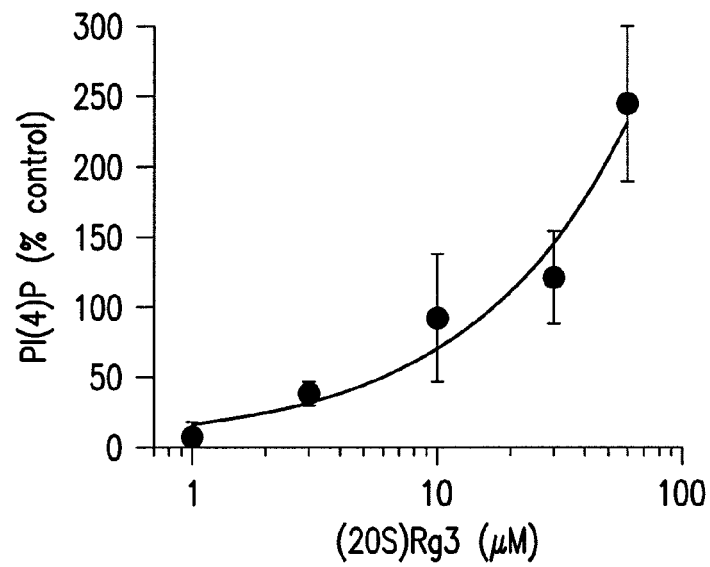
Figure 10F:
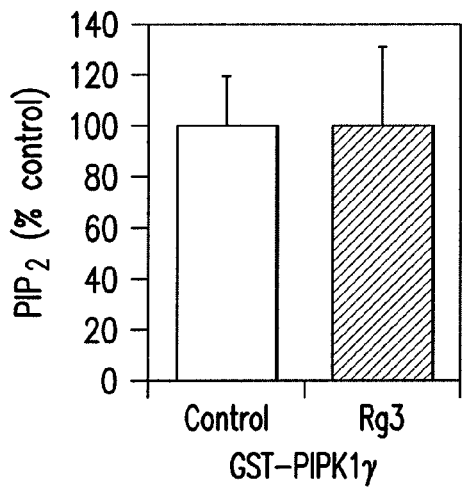

Incubation of 50 µM (20S)Rg3 with purified enzyme enhanced PI4KIIα activity in a dose-dependent manner (FIG. 10E). In contrast, (20S)Rg3 did not confer any detectable effects on the activity of PIPK1γ, a major brain PIP 5-kinase, at 50 µM (FIG. 10F). Incubating both PI4KIIα (PI 4-kinase) and PIPK1γ (PI 5-kinase) with (20S)Rg3 led to an increase of both PIP and PIP2, suggesting that the (20S)Rg3-mediated increase of PIP2 is likely to be mediated by enhanced synthesis of PIP via the activation of PI4KIIα. Thus, (20S)Rg3 serves as an activator of PI4KIIα, resulting in the increase in the steady-state levels of PIP and subsequently the levels of PIP2.

11. EXAMPLE

Effect of (20S)Rg3 and PI4K on Aβ42 and its Toxicity

Since Aβ42 oligomers induce the reduction in PIP2 levels in neurons, the use of a PIP/PIP2-promoting agent, such as (20S)Rg3, was tested to determine whether the agent can reverse or prevent the Aβ42-oligomer-induced PIP2 reduction. Treatment of cultured neurons with (20S)Rg3 inhibited the reduction in PIP2 levels by Aβ42 oligomer. See FIG. 11A. Furthermore, treatment of cultured neurons with (20S)Rg3 also inhibited the increase in PA levels induced by oAβ42. Thus, when cultured neurons are co-treated with (20S)Rg3 and Aβ42 oligomers, Aβ42 oligomer-induced reduction in PIP2 levels can be inhibited. See FIG. 11B. When cells were pre-incubated with (20S)Rg3, Aβ42 oligomer-induced PIP2 reduction was also blocked efficiently.

Next, experiments were performed to determine whether (20S)Rg3 treatment can inhibit Aβ-induced PIP2 turnover at the plasma membrane. As described previously (72) the binding of a PIP2 sensor (GFP-PHPLCδ1) decreased at the plasma membrane in response to Aβ42 oligomer treatment. The binding of GFP-PHPLCδ1 at the plasma membrane is expressed as a ratio of fluorescence at the plasma membrane to cytosolic fluorescence. Co-incubation of Aβ oligomers with (20S)Rg3 prevented the loss of the plasma membrane fluorescence. (FIG. 12A). These data suggest that (20S)Rg3 protects against the Aβ oligomer-induced loss of PIP2 from the plasma membrane by increasing the basal levels of PIP2 in these cells. (20S)Rg3 did not exert its protective effects by interacting with Aβ oligomer directly, since (20S)Rg3 had no effects on the oligomerization process of Aβ42. It was observed that co-incubation of (20S)Rg3 (10 µM) with Aβ oligomers resulted in normal LTP, indicating that (20S)Rg3 antagonizes Aβ-induced synaptic dysfunction (FIG. 12B).

Abundant evidence indicates that Aβ-associated synaptic dysfunction results in memory impairments in AD animal models (73, 74, 75). Therefore experiments were performed to determine whether (20S)Rg3 can improve the memory impairments in an AD mouse model. (20S)Rg3 was administered for three weeks (i.p., 10 mg/kg) to 3 month-old APP/PS1 mice and age-matched littermate controls. Mice were then subjected to behavioral testing in the radial-arm water-maze paradigm (74). Previous studies showed that APP/PS1 mice exhibit spatial working memory impairments at the age of 3-months, which correlate with soluble Aβ levels but not with amyloid plaque load (76,77). (20S)Rg3 administration dramatically improved spatial working memory deficits in APP/PS1 mice (FIG. 12C).

Since (20S)Rg3 potentiates PI4KIIα activity (conversion from PI to PIP), it was determined whether the increase in PI4KIIα activity exerts similar effects on Aβ42 generation as observed in the (20S)Rg3-treated cells. Overexpression of PI4KIIα leads to increased protein levels of PI4KIIα and increased PI 4-kinase activity as measured by lipid kinase assay. Aβ42 generation was significantly down-regulated (~40% in CHO cells, FIG. 13A; ~80% in neuro2a cells) in cells transfected with wild-type PI4KIIα, but not with kinase-dead mutant PI4KIIα, suggesting that the catalytic activity of PI4KIIα is required for the observed Aβ42 reduction in the PI4KIIα-overexpressing cells. Treatment of the PI4KIIα-overexpressing cells with (20S)Rg3 conferred additive effects on Aβ42 reduction (FIG. 13B). Thus, increased levels of the (20S)Rg3 target protein PI4KIIα may amplify the effects of the Aβ42-lowering activity of (20S)Rg3.

Figures 14A, 14B:
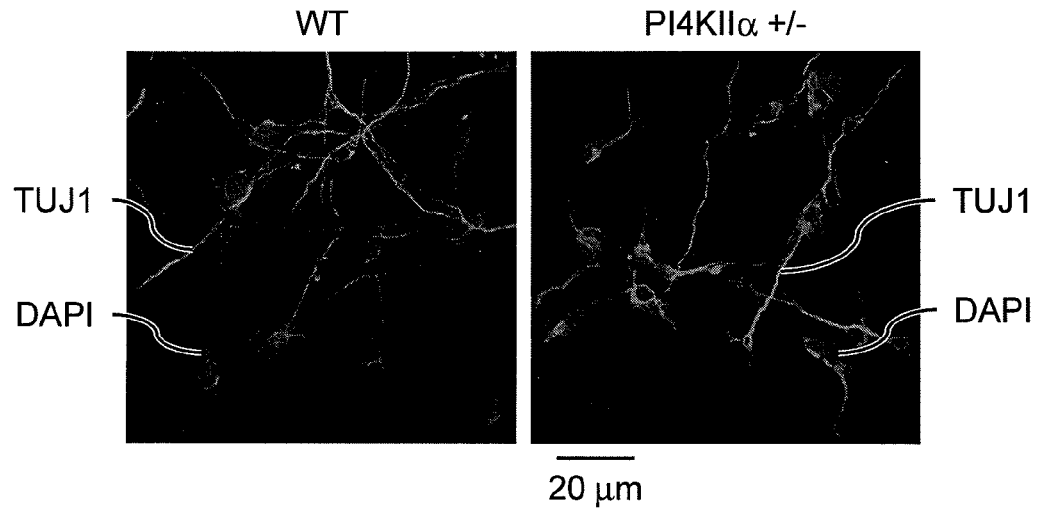
Figures 14C, 14D:
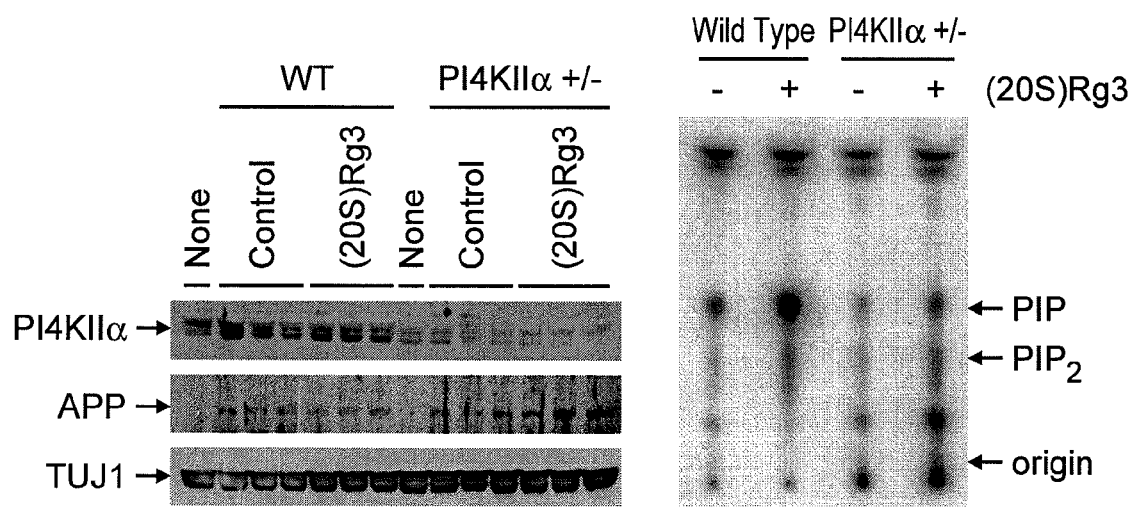
Figure 14E:
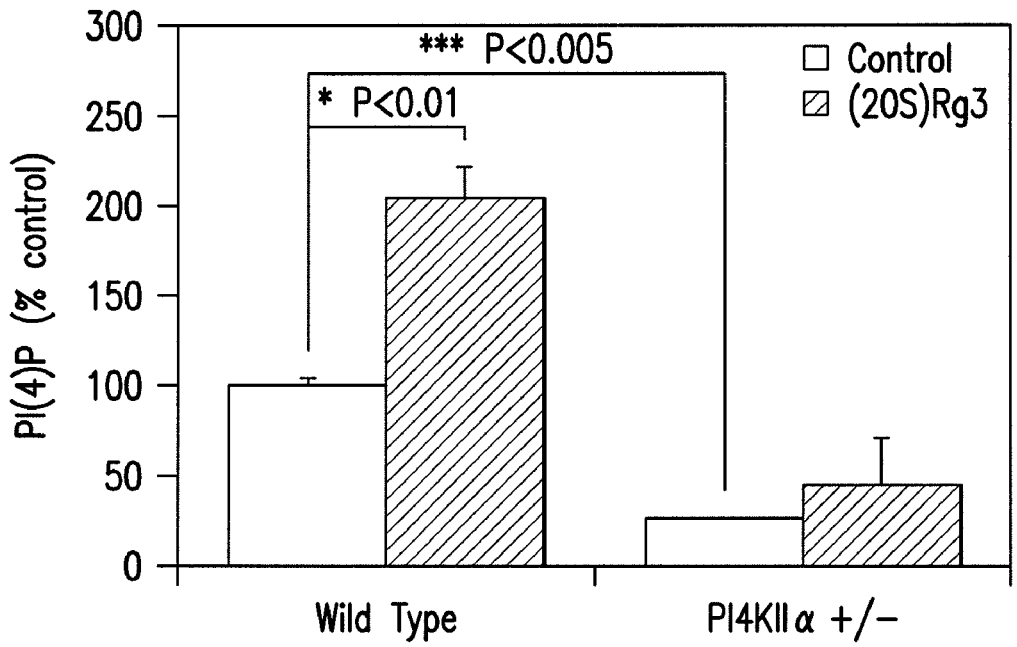
Figure 14F:
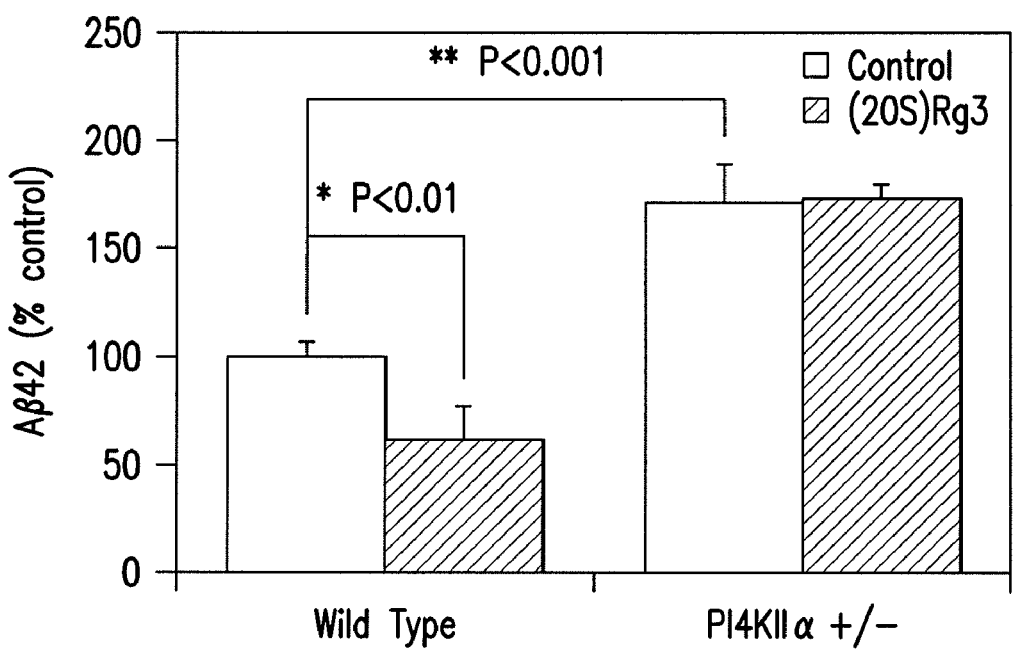

Mouse embryonic stem (ES) cell-derived pyramidal neurons that harbor the heterozygote knockout of the PI4KIIα allele (PI4KIIα +/−; purchased from Sanger Institute Gene Trap Resource; http://www.sanger.ac.uk/PostGenomics/genetrap/) were then used to further study the role for PI4KIIα in Aβ42 generation in neurons. Differentiation and morphology of pyramidal neurons from PI4KIIα heterozygote (+/−) ES cells were indistinguishable from those from match wild-type ES cells (representative neuronal staining is shown in FIGS. 14A and B). Among several putative ES cell clones, two clonal lines (AC37 and AD14) were identified which were found to express significantly reduced amounts of PI4KIIα protein detected by Western blot analysis (FIG. 14C). Lipid kinase activity assay and TLC analysis revealed that PI 4-kinase activity was significantly reduced in these lines (FIG. 14D,E). Interestingly, (20S)Rg3-induced PIP synthesis was substantially reduced, indicating the reduced PI4KIIα activity in these lines (and no compensatory increases in PI 4-kinase activity). Aβ42 generation was substantially elevated in the neurons derived from PI4KIIα +/−ES cells. Thus, together with the PI4KIIα overexpression results (FIG. 13B), these data suggest that PI4KIIα activity may be inversely correlated with Aβ42 production in neurons. Interestingly, in the PI4KIIα +/−ES-derived neurons, (20S)Rg3 was no longer able to reduce Aβ42 (FIG. 14F), indicating that the Aβ42-lowering activity of (20S)Rg3 needs normal expression of PI4KIIα.

12. EXAMPLE

Effect of (20S)Rg3 and PI4KIIα on the Association of Presenilin-1 with Lipid Rafts The PIP/PIP2-promoting compound (20S)Rg3 modulates the association of presenilin 1 (PS1) fragments with lipid rafts. An experimental protocol to separate PS1 from the γ-secretase complex-containing lipid raft fractions was established.

Lipid rafts were isolated from cultured neurons following detergent solubilization using polyoxyethylene(20) oleyl ether (available as BRIJ 98™ from Sigma-Aldrich, St. Louis, Mo.) at 37° C. Briefly, Cells grown to confluence in two 150 mm dishes were washed twice with ice-cold phosphate buffer saline, scraped into 1 ml of lysis buffer, containing polyoxyethylene(20) oleyl ether (available as BRIJ 98™ from Sigma-Aldrich, St. Louis, Mo.), supplemented with a protease inhibitor tablet (Roche), and lysates incubated at 37° C. Solubilized cell lysate was then adjusted to contain 40% final concentration of sucrose (final volume, 2 mL) in ultracentrifuge tube. A discontinous sucrose gradient was then formed by the addition of 35% sucrose (6 ml) and 5% sucrose (4 ml), and centrifuged at 39,000 rpm for 18 hr in SW41 rotor (Beckman Ins.) at 4° C. (fraction 1-top to fraction 12-bottom). Twelve 1 ml fractions were collected starting with the top of the gradient and equal volumes of each fraction were analyzed by Western blotting. For further information regarding purification of lipid rafts, see Ref. 110.

When the levels of PS1 C-terminal fragments (PS1-CTF) were measured in HeLa cells, the lipid raft-associated PS1-CTF levels were found to be significantly reduced, while total PS-CTF levels were unchanged in cells treated with (20S)Rg3 (FIG. 15 B,C). These data (reduced PS1-CTF in the raft fraction) were highly reproducible in at least two additional cell types (CHO and neuro2a) as well as the brain tissues from the mice treated with (20S)Rg3. In contrast, previously reported selective Aβ42 inhibitors (e.g. a subset of NSAIDs, such as sulindac sulfide; 78) did not confer any effects on the association of PS1 fragments with lipid rafts. These data suggest that the mechanism of action of (20S)Rg3 and sulindac sulfide may be different, further raising the possibility that the PIP/PIP2-promoting activity of (20S)Rg3 may modulate a localized pool of lipids and subsequently alter the association of PS1-CTF with lipid rafts.

Figure 15A:
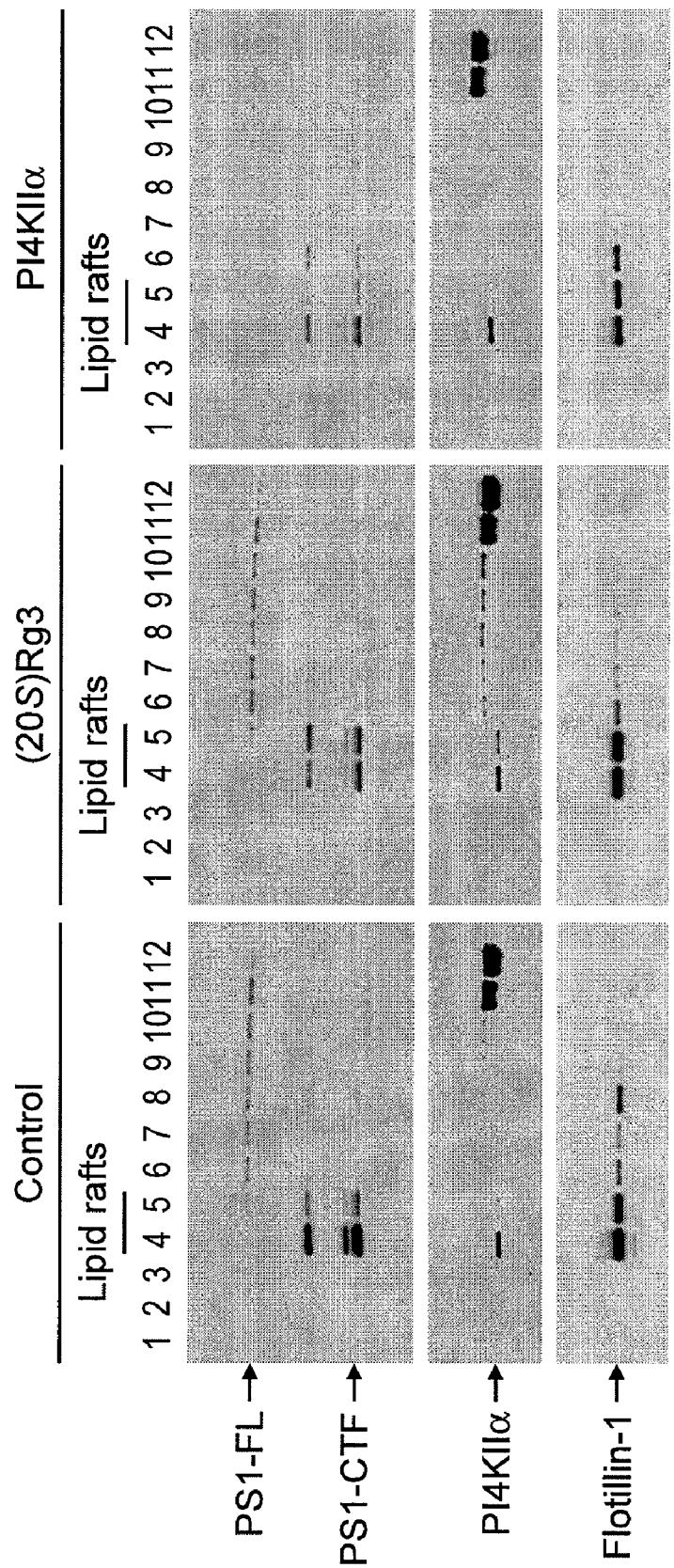
Figure 15B:
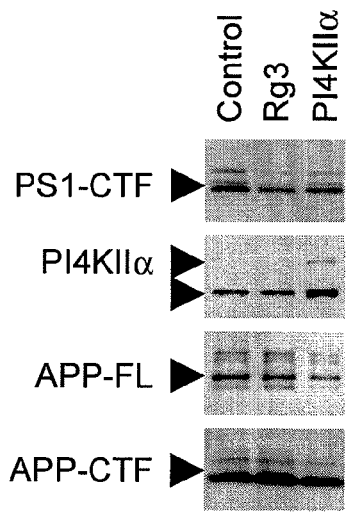
Figure 15C:
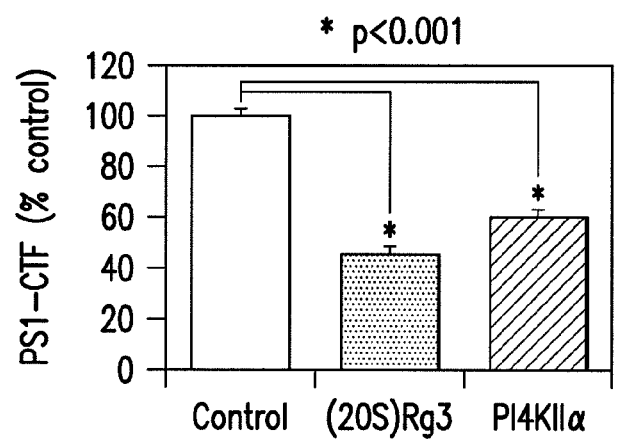
Figure 15D:
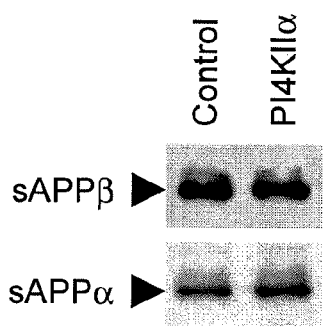
Figure 15E:
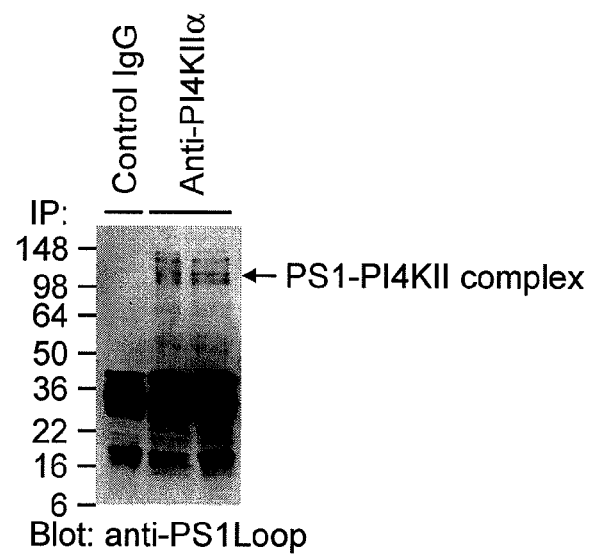

To determine if the PIP/PIP2-enhancing activity of (20S) Rg3 is involved with the changes in the association of PS1 fragments with lipid rafts, the effects of PI4KIIα overexpression on the lipid raft association of PS1 fragments was tested. It was found that overexpression of PI4KIIα (but not the KD mutant) causes the reduction of PS1 association with the lipid raft fraction (FIG. 15A,B,C), suggesting that PI 4-kinase activity is likely to be responsible for the biochemical redistribution of PS1 out of lipid rafts. The effects of PI4KIIα were selective to Aβ42 generation and PS1 redistribution since PI4KIIα didn't affect the secretion of β-secretase and α-secretase-derived soluble APP (sAPPβ and sAPPα, respectively) (FIG. 15D). As previously reported, PI4KIIα was detected in the lipid raft fractions (79-83) and was co-distributed with PS1-CTF and flotillin (a raft marker) (FIG. 15A). Chemical cross-linking experiments followed by co-immunoprecipitation showed that PS1 and PI4KIIα form a stable complex (FIG. 15E). Thus, these data suggest that both (20S) Rg3 treatment and PI4KIIα expression may modulate both the association of PS1-CTF with lipid rafts and Aβ42 secretion via a mechanism involving increased levels of PIP/PIP2. These findings also raise the possibility that the PIP/PIP2-promoting activity may influence the lipid composition of presenilin-harboring lipid rafts and therefore control the lipid microenvironment of PS1/γ-secretase, which has been shown to influence Aβ42-producing γ-secretase activity (84, 85).

13. EXAMPLE

Phosphoinositide Levels in Alzheimer's Patients

Altered phosphoinositide metabolism in brains of human AD patients. To explore possible defects in phospholipids metabolism, lipid kinase assays were performed using ATP-γ[P32]. See FIG. 16A-C. Lipid kinase-mediated incorporation of radiolabeled phosphate groups was visualized using thin layer chromatography (TLC) followed by phosphoimaging. It was found that phosphoinositide metabolism of phosphatidic acid (PA) was substantially reduced in AD samples as compared to control groups. See FIG. 16A. In contrast, PI(4)P labeling pattern was indistinguishable between AD and control samples. See FIG. 16B. These changes were not due to different age or post-mortem intervals since neither age of the patients nor changes in PMI correlate with the changes in the metabolism of phosphoinositides (PIs) and PA. PIP2 labeling patterns are also affected. See FIG. 16C. Thus, alteration of PA metabolism (and PIP2) may be used a foundation to design a novel biomarker for AD.

14. EXAMPLE

Effects of Inhibiting PI3-Kinase

N2a cells stably expressing human APP with the Swedish mutation were grown in DMEM-supplemented with 50% Opti-MEM, 10% FBS, penicillin, streptomycin, and G418. Cells were grown to 80-90% confluence and treated for 6 hours with the drugs as indicated in 900 µl media. The conditioned media was harvested and centrifuged for 15 minutes at 14,000 rpm in a table top Eppendorf centrifuge 5417R. The adherent cells were washed two times with ice cold PBS and lysed in 100 μl super IP buffer (10 mM Tris Cl, pH, 7.4, 150 mM NaCl, 2 mM EDTA, 1% Triton X-100, 0.25% NP-40, protease inhibitors). Cell lysates were scraped and incubated for 15 minutes on ice before centrifugation at 14,000 rpm in a table-top Eppendorf centrifuge 5417R. Cleared conditioned media and lysates were stored at −80° C. until use. Aβ 42 and Aβ40 were quantified with the commercially available kit from Biosource as indicated in the protocol. Protein concentration of the cell lysate was determined using the BCA assay from Pierce. Pan inhibitors of PI3Ks, wortmannin and LY-294002, were able to inhibit the production of Aβ42 from N2a cells stably over-expressing human APP with the Swedish mutation (FIG. 17).

KU-55933 is a small molecule inhibitor of ATM kinase as well as PI3K family members (FIG. 22). KU-55933 was observed to inhibit the production of Aβ42 (FIG. 18) as well as Aβ40 at concentrations much lower than LY-294002, with an EC50 of 3.5 μM. In these experiments, N2a cells stably expressing human APP with the Swedish mutation were treated for 6 hours with KU-55933 (also referred to as SMT5) at the concentrations indicated in 900 μl media. The conditioned media was harvested as described above and cell lysates were collected. Aβ 42 and Aβ40 were quantified with the commercially available kit from Biosource as indicated in the protocol. Protein concentration of the cell lysate was determined using the BCA assay from Pierce.

At a comparable concentration, KU-55933 (SMT5) also rescued the depletion of PIP2 caused by treatment with Aβ42 oligomers in a neuronal model cell line PC12 cells (FIG. 19). PC12 cells were cultured in RPMI media supplemented with 1 mM glutamine, 5% FBS, 10% horse serum and penicillin, streptomycin. The day before transfection, PC12 cells were split 50% and plated on poly-D-lysine coated coverslips. Cells were transfected with Lipofectamine 2000 as per the manufacturer's protocol with GFP-PH$_{PLC\delta1}$. After 16-24 hours, cells were treated as indicated for 30 minutes in conditioned media. Cells were then briefly washed in PBS and fixed for 20 minutes in 4% paraformaldehyde. Cells were then washed in 0.1M glycine and twice in PBS for 5 minutes each. Cells were mounted using Vectashield. Images were collected using a con-focal microscope and the plot profile was analyzed with ImageJ 1.37v. The ratio of the fluorescence profiles of the plasma membrane and the cytosol were calculated and deemed to represent translocation of the PIP2 probe GFP-PH-PLCδ1 (72).

At concentrations which caused a decrease in the Aβ42 generation, SMT5 did not induce caspase 3 cleavage indicating that cells were not undergoing apoptosis triggered by either intrinsic or the extrinsic pathways (FIG. 20). The compound KU-55933 was found not to be cytotoxic in previous studies (113, 114). Western blot analysis of full length APP and caspase3 was conducted on 30 μg of lysate collected as described above from N2a cells stably expressing APP harboring the Swedish mutation. Cells were treated for 6 hours with KU-55933 at concentrations indicated. APP was detected using the LN27 antibody from Zymed and caspase 3 full length and cleavage product were probed using the caspase 3 antibody from Cell Signaling Technology.

It was found that PI3K inhibitors LY-294002, wortmannin, and KU-55933 all inhibit the production of Aβ42 thus making PI3Ks a therapeutic target for Alzheimer's disease. KU-55933 was able to partially rescue the Aβ42 oligomer induced depletion of PIP2 suggesting the action of KU-55933 may involve, but is not limited to, the stabilization of PIP2 at the plasma membrane. PI3K inhibition may lead to stabilization of PIP2 at the plasma membrane and ameliorate Alzheimer's disease pathologies by decreasing the production of Aβ42 and preventing Aβ42 oligomer induced synaptic dysfunction.

15. EXAMPLE

Overexpression of PI4-Phosphatases

Overexpression of TMEM55A or TMEM55B leads to the elevated Aβ42 (FIG. 21).

16. REFERENCES

1. Hardy J (1997). Amyloid, the presenilins and Alzheimer's disease. Trends Neurosci. 20, 154-159.
2. Tanzi R E (1999). A genetic dichotomy model for the inheritance of Alzheimer's disease and common age-related disorders. J. Clin. Invest. 104, 1175-1179.
3. Selkoe D J (2001). Alzheimer's disease: genes, proteins, and therapy. Physiol. Rev. 81, 741-766.
4. Selkoe D J and D Schenk (2003). Alzheimer's disease: molecular understanding predicts amyloid-based therapeutics Annu. Rev. Pharmacol. Toxicol. 43, 545-584.
5. Kim S H et al. (2000). Subcellular localization of presenilins: association with a unique membrane pool in cultured cells. Neurobiol. Dis. 7, 99-117.
6. Kaether C et al. (2002). Presenilin-1 affects trafficking and processing of betaAPP and is targeted in a complex with nicastrin to the plasma membrane. J. Biol. 158 (3), 551-561.
7. Thinakaran G et al. (1996). Endoproteolysis or presenilin 1 and accumulation of processed derivatives in vivo. Neuron 17, 181-190.
8. Kim T W et al. (1997). Endoproteolytic processing and proteasomal degradation of presenilin 2 in transfected cells. J. Biol. Chem. 272, 11006-111010.
9. Seeger M et al. (1997). Evidence for phosphorylation and oilgomeric assembly of presenilin 1. Proc. Natl. Acad. Sci. U.S.A. 94, 5090-5094.
10. Kimberly W T et al. (2000). The transmembrane aspartates in presenilin 1 and 2 are obligatory for -secretase activity and amyloid-protein generation. J. Biol. Chem. 275, 3173-3178.
11. Esler W P 35 et al (2000). Transition-state analogue inhibitors of-secretase bind directly to presenilin-1. Nat. Cell. Biol. 2, 1-7.
12. Li Y M et al. (2000). Photoactivated-secretase inhibitors directed to the active site covalently label presenilin 1. Nature 405, 689-693.
13. Wolf M S et al. (1999). Are presenilins intramembrane-cleaving proteases? Implication for the molecular mechanism of Alzheimer's disease. Biochemistry 38, 11223-11230.
14. Scheuner D et al. (1996). Secreted amyloid-protein similar to that in senile plaques of Alzheimer's disease is increased in vivo by the presenilin 1 and 2 and APP mutations linked to familial Alzheimer's disease. Nat. Medicine 2, 864-870.
15. Czech C. Tremp G. and L Pradier (2000). Presenilins and Alzheimer's disease: biological functions and pathogenic mechanisms. Prog Neurobiol. 60(4), 363-384.
16. Etcheberrigaray R. et al. (1998). Calcium responses in fibroblasts from asymptomatic members of Alzheimer's disease families. Neurobiol. Dis. 5, 37-45.
17. Ito E et al. (1994). Internal Ca+2 mobilization is altered in fibroblasts from patients with Alzheimer's disease. Proc. Natl. Acad. Sci. USA 91, 534-538.

18. Leissring M A et al. (2001). Subcellular mechanisms of presenilin-medicated enhancement of calcium signaling. Neurobiol. Dis. 8, 49-478.
19. Guo Q et al. (1996). Alzheimer's PS-1 mutation perturbs calcium homeostatsis and sensitizes PC12 cells to death induced by amyloid b-peptide. Neuroreport 8, 379-383.
20. Schneider et al. (2001). Mutant presenilins disturb neuronal calcium homeostasis in the brain of transgenic mice, decreasing the threshold for excitotoxicity and facilitating long-term potentiation. J. Biol. Chem. 276, 11539-1154.
21. Yoo A S et al. (2000). Presenilin-mediated modulation of capacitative calcium entry. Neuron 27, 561-572.
22. Leissring M A et al. (2000). Capacitative calcium entry deficits and elevated luminal calcium content in mutant presenilin-1 knockin mice. J. Cell Biol. 149, 793-798.
23. Herms J. et al. (2003). Capacitative calcium entry is directly attenuated by mutant presenilin-1, independent of the expression of the amyloid precursor protein. J. Biol. Chem. 278, 2484-2489.
24. Thinakaran G and A T Parent (2004). Identification of the role of presenilins beyond Alzheimer's disease. Pharm. Res. 50, 411-418.
25. Williams R L (1999). Mammalian phosphoinositide-specific phospholipase C. Biochim. Biophys. Acta 1441, 255-267.
26. Rhee S G and Y S Bai (1997). Regulation of phosphoinostitide-specific phospholipase C isozymes. J. Biol. Chem. 272(24), 15045-15048.
27. Katan M (1998). Families of phosphoinositide-specific phospholipase C structure and function. Biochim. Biophys. Acta 1436, 5-17.
28. Kim D et al. (1997). Phospholipase C isozymes selectively couple to specific neurotransmitter receptors. Nature 389, 290-293.
29. Delmas P. Crest M and D A Brown (2004). Functional organization of PLC signaling microdomains in neurons. Trend Neurosci 27(1), 41-47.
30. Hilgemann D W, Feng S and C Nasuhoglu (2001). The complex and intriguing lives of PIP2 with ion channels and transporters, STKE 111, 1-8.
31. Shimohama S et al. (1998). Phospholipase C isozymes in the human brain and their changes in Alzheimer's disease. Neuroscience 82(4), 999-1007.
32. Zhang D et al. (1998). Regional levels of brain phospholipase Cgamma in Alzheimer's disease Brain Res. 811(1-2), 161-165.
33. Ferrari-DiLeo G and D D Flynn (1993). Diminished muscarinic receptor-stimulated [3H]-PIP2 hydrolysis in Alzheimer's disease. Life Sci. 53(25), PL439-444.
34. Crews F T, Kurian P and G Freund (1994). Cholinergic and serotonergic stimulation of phosphoinositide hydrolysis is decreased in Alzheimer's disease. Life Sci. 55(25-26), 1993-2002.
35. De Sarno P et al. (2000). Alterations in muscarinic receptor-coupled phosphoinostitide hydrolysis and AP-1 activation in Alzheimer's disease cybrid cells. Neurobiol. Agin21(1), 31-38.
36. Runnels L W, Yue L, and Clapham D E (2002). The TRPM7 channel is inactivated by PIP2 hydrolysis. Nature Cell Biology 4, 329-336.
37. Wrigley et al. (2005). Functional overexpression of-secretase reveals protease-independent trafficking functions and a critical role of lipids for protease activity. J Biol. Chem. 280(13), 12523-12535.
38. Wenk M R et al. (2001). PIP kinase 1 is the major PI(4,5)P2 synthesizing enzyme at the synapse. Neuron 32, 79-88.
39. Di Paolo G et al. (2004). Impaired PtdIns(4,5)P2 synthesis in nerve terminals produces defects in synaptic vesicle trafficking. Nature 431, 415-422.
40. Cremona O et al. (1999). Essential role of phosphoinositide metabolism in synaptic vesicle recycling. Cell 99(2), 179-188.
41. Martinat C et al. (2004). Sensitivity to oxidative stress in DJ-1 deficient dopamine neurons: an ES-derived cell model of primary Parkinsonism. PLoS Biology 2 (11), e327.
42. Bibel M et al. (2004). Differentiation of mouse embryonic stem cells into a defined neuronal lineage. Nature Neurosci. 7(9), 1003-1009.
43. Stpyridis M P and A G Smith (2003). Neural differentation of mouse embryonic stem cells. Biochem Soc. Trans. 31(1), 45-49.
44. Xian H Q et al. (2003). Subset of ES-cell-derived neural cells marked by gene targeting. Stem Cells 21, 41-49.
45. Abe Y et al. (2003). Analysis of neurons created from wild-type and Alzheimer's mutation knock-in-embryonic stem cells by a highly efficient differentiation protocol. J. Neurosci 23 (24), 8513-8525.
46. Kim S H et al. (2001). Multiple effects of aspartate mutant presenilin 1 on the processing and trafficking of anyloid precursor protein. J. Biol. Chem. 276(46), 43343-43350.
47. Pendaries C. et al. (2003). Phosphoinositide signaling disorders in human diseases. FEBS Lett. 546(1):25-31.
48. Brewer, G. J. & Cotman, C. W. (1989) Survival and growth of hippocampal neurons in defined medium at low density: advantages of a sandwich culture technique or low oxygen. Brain Res. 494, 65ÿ74.
49. Hurley and Meyer (2001). Subcellular targeting by membrane lipids, Curr. Opin. Cell Biol. 13(2):146-152.
50. Lemon et al. (2003). Metabolic receptor activation, desensitization and sequestration I: modeling calcium and inositol 1,4,5 trisphosphate dynamics following receptor activation. J. Theoret. Biol. 223(1):93-111.
51. Lemon et al. (2003). Metabolic receptor activation, desensitization and sequestration II: modeling calcium and inositol 1,4,5 trisphosphate dynamics following receptor activation. J. Theoret. Biol. 223(1):113-129.
52. McLaughlin et al. (2002). PIP2 and proteins: interactions, organization, and information flow. Annu. Rev. Biophys. Biomol. Struct. 31:151-175.
53. Miki et al. (1996). N_WASP, a novel actin-depolymerizing protein, regulates the cortical cytoskeletal rearrangement in a PIP2 dependent manner downstream of tyrosine kinases. EMBO J. 15(9):5326-5335.
54. Papayannopoulos et al. (2005). A polybasic motif allows N-WASP to act as a sensor of PIP2 density. Mol. Cell 17(2):181-191.
55. Giantonio B et al. (2004) Phase I and Pharmacokinetic Study of the Cytotoxic Ether Lipid Ilmofosine Administered by Weekly Two-Hour Infusion in Patients with Advanced Solid Tumors. Clinical Cancer Res. 10: 1282-1288.
56. Croft S L et al. (1993). Antileishmanial activity of the ether phospholipid ilmofosine. Trans R Soc Trop Med. Hyg. 87(2):217-219.
57. Principe P. et al. (1994). Tumor Cell Kinetics Following Long-Term Treatment with Antineoplastic Ether Phospholipids. Cancer Detection and Prevention 18(5):393-400.
58. Haufe G and Burchardt A (2001). Synthesis of a Fluorinated Ether Lipid Analogous to a Platelet Activating Factor. Eur. J. Organic Cem. 23:4501-4507.

59. Schmid A and Woscholski R (2004). Phosphatases as small molecule target: inhibiting the endogenous inhibitors of kinases. Biochem. Soc. Trans. 32 (part 2):348-349.
60. Shingu T et al. (2003). Growth inhibition of human malignant glioma cells induced by the PI3-K-specific inhibitor. J. Neurosurg. 98(1): 154-161.
61. Berdel W et al., (1987). Clinical phase I pilot study of the alkyl lysophospholipid derivative ET-18-OCH3. Lipids 22(11):967-999.
62. Halet G et al. (2002). The dynamics of plasma membrane PtdIns(4,5)P(2) at fertilization of mouse eggs. J Cell Sci. 115(Pt 10):2139-49.
63. Stokes C E and J N Hawthorne (1987). Reduced phosphoinositide concentration in anterior temporal cortex of Alzheimer-diseased brains. J Neurochem 48(4):1018-21.
64. Lee et al. (1995). Amyloid precursor protein processing is stimulated by metabotropic glutamate receptors. Proc Natl Acad Sci USA 92(17):8083-7.
65. Nitsch R M et al. (1996). Serotonin 5-HT2a and 5-HT2c receptors stimulate amyloid precursor protein ectodomain secretion. J Biol Chem 271(8):4188-94.
66. Berkovic D (1998). Cytotoxic etherphospholipid analogues. Gen. Pharmacol. 31(4):511-517.
67. Braak H and Braak E (1991). Demonstration of amyloid deposits and neurofibrillary changes in whole brain sections. Brain Pathol. 1(3):213-216.
68. Morrison J H and H of P R (1997). Life and death of neurons in the aging brain. Science 278(5337):412-419.
69. Nashuhoglu et al. (2002). Anal. Biochem. 301, 243-254.
70. DiPaolo et al. (2004). Nature 431, 415-422.
71. Landman et al (2006) Presenilin mutations linked to familial Alzheimer's disease cause an imbalance in phosphatidylinositol 4,5-bisphosphate metabolism. Proc Natl Acad Sci USA. 103(51):19524-9.
72. Balla and Vamai (2002). Visualizing cellular phosphoinositide pools with GFP-fused protein modules. Sci STKE Mar. 26, 2002(125), p13.
73. Selkoe (2002). Alzheimer's disease is a synaptic failure. Science 298, 789-791.
74. Gong et al. (2006). Ubiquitin hydrolase Uch-LI rescues beta-amyloid induced decreases in synaptic function and contextual memory. Cell 126, 775-788.
75. Hsiao et al. (1996). Correlative memory deficits, A beta elevation, and amyloid plaques in transgenic mice. Science 274, 99-102.
76. Holcomb et al. (1998). Accelerated Alzheimer-type phenotype in transgenic mice carying both mutant amyloid precursor protein and presenilin 1 transgenes. Nat. Med. 4, 97-100.
77. Trinchese et al. (2004). Progressive age-related development of Alzheimer-like pathology in APP/PS1 mice. Ann. Neurol. 55(6), 801-814.
78. Weggen et al. (2001). A subset of NSAIDs lower amyloidogenic Abeta42 independently of cyclooxygenase activity.
79. Wang et al. (2003). Phosphatidylinositol 4 phosphate regulates targeting of clathrin adaptor AP-1 complexes to the Golgi. Cell 114, 299-310.
80. Salazar et al., (2005). Phosphatidylinositol-4-kinase type II alpha is a component of adaptor protein-3-derived vesicles. Mol. Biol. Cell 16, 3692-3704.
81. Pike (1999). Phosphatidylinositol 4-kinases and the role of polyphosphoinositides in cellular regulation. Endocr. Rev. 13, 692-706.
82. Minogue et al. (2006). Phosphatidylinositol 4-kinase is required for endosomal trafficking and degradation of the EGF receptor. J. Cell Sci. 119, 571-581.
83. Balla et al. (2002). Characterization of type II phosphatidylinositol 4-kinase isoforms reveals association of the enzymes with endosomal vesicular compartments. J. Biol. Chem. 277, 20041-20050.
84. Kern et al. (2006). Down-regulation of endogenous amyloid precursor protein processing due to cellular aging. J Biol. Chem. (2006) February 3; 281(5):2405-13. Erratum in: J Biol. Chem. 2006 May 5; 281(18):13000.
85. Grimm et al. (2005). Regulation of cholesterol and sphingomyelin metabolism by amyloid-beta and presenilin. Nat Cell Biol. November; 7(11): 1118-23. Erratum in: Nat Cell Biol. 2006 April; 8(4):424.
86. Hennessey et al. (2005). Exploiting the PI3K/AKT pathway for cancer drug discovery. Nat Rev Drug Discov. December; 4(12):988-1004.
87. Katso et al. (2001). Cellular function of phosphoinositide 3-kinases: implications for development, homeostasis, and cancer. Annu Rev Cell Dev Biol.; 17:615-75.
88. Wymann and Pirola (1998). Structure and function of phosphoinositide 3-kinases. Biochim Biophys Acta. 1998 Dec. 8; 1436(1-2):127-50.
89. Ruckle et al. (2006). PI3 Kgamma inhibition: towards an 'aspirin of the 21st century'? Nat Rev Drug Discov. November; 5(11):903-18.
90. Knight et al. (2006). A pharmacological map of the PI3-K family defines a role for p110alpha in insulin signaling. Cell. May 19; 125(4):733-47
91. Fan et al. (2006). A dual PI3 kinase/mTOR inhibitor reveals emergent efficacy in glioma. Cancer Cell. May; 9(5):341-9.
92. Jackson et al. (2005). PI 3-kinase p110beta: a new target for antithrombotic therapy. Nat. Med. May; 11(5):507-14.
93. Sadhu et al. (2003), Selective role of PI3K delta in neutrophil inflammatory responses. Biochem Biophys Res Commun. September 5; 308(4):764-9.
94. Camps et al. (2005). Blockade of PI3 Kgamma suppresses joint inflammation and damage in mouse models of rheumatoid arthritis. Nat. Med. September; 11(9):936-43.
95. Barber et al. (2005). PI3 Kgamma inhibition blocks glomerulonephritis and extends lifespan in a mouse model of systemic lupus. Nat. Med. September; 11(9):933-5.
96. Pei et al. (2003). Role of protein kinase B in Alzheimer's neurofibrillary pathology. Acta Neuropathol (Berl). April; 105(4):381-92.
97. Griffin et al. (2005). Activation of Akt/PKB, increased phosphorylation of Akt substrates and loss and altered distribution of Akt and PTEN are features of Alzheimer's disease pathology. J. Neurochem. April; 93(1): 105-17
98. Rickle et al. (2004). Akt activity in Alzheimer's disease and other neurodegenerative disorders. Neuroreport. April 29; 15(6):955-9
99. Weihl et al. (1999). Mutant presenilin-1 induces apoptosis and downregulates Akt/PKB. J. Neurosci. 1999 Jul. 1; 19(13):5360-9
100. Kang et al. (2005). Presenilins mediate phosphatidylinositol 3-kinase/AKT and ERK activation via select signaling receptors. Selectivity of PS2 in platelet-derived growth factor signaling. J Biol. Chem. September 9; 280 (36):31537-47.
101. Zhang et al. (2007). Presenilins regulate the cellular level of the tumor suppressor PTEN. Neurobiol Aging. 2007 Jan. 12

102. Baki et al. (2004). PS1 activates PI3K thus inhibiting GSK-3 activity and tau overphosphorylation: effects of FAD mutations. EMBO J. July 7; 23(13):2586-96

103. Tesco et al. (2000). GSK3 beta forms a tetrameric complex with endogenous PS1-CTF/NTF and beta-catenin. Effects of the D257/D385A and FAD-linked mutations. Ann N Y Acad. Sci. 920:227-32

104. Twomey et al. (2006). Presenilin-1 is an unprimed glycogen synthase kinase-3beta substrate. FEBS Lett. July 24; 580(17):4015-20.

105. Kirschenbaum *(2001).

106. Petanceska and Gandy (1999). The phosphatidylinositol 3-kinase inhibitor wortmannin alters the metabolism of the Alzheimer's amyloid precursor protein. J Neurochem. December; 73(6):2316-20

107. Phiel et al. (2003). GSK-3alpha regulates production of Alzheimer's disease amyloid-beta peptides. Nature. May 22; 423(6938):435-9.

108. Su et al. (2003). Lithium, a common drug for bipolar disorder treatment, regulates amyloid-beta precursor protein processing. Biochemistry. June 8; 43(22):6899-908.

109. Ungewickell et al. (2005) The identification and characterization of two phosphatidylinositol-4,5-bisphosphate 4-phosphatases. Proc Natl Acad Sci USA. 102(52):18854-9

110. Vetrivel et al. (2004), J. Bio. Chem. 279(43):44945-44954.

111. Ruckle et al., Nature Review Drug Discovery, 5:903-918

112. Knight et al. (2006), Cell 125, 733-747.

113. Cowell et al. (2005), Sensitization of breast carcinoma cells to ionizing radiation by small molecule inhibitors of DNA-dependent protein kinase and ataxia mutated . . . . Biochem. Pharmacol. 71(1-2), 13-20.

114. Lau et al. (2005), Suppression of HIV-1 infection by a small molecule inhibitor of the ATM molecule. Natl. Cell. Biol. 7(5), 493-500.

115. Vandeput et al. (2007), Biphenyl 2,3',4,5',6-pentakisphosphate, a novel inositol polyphosphate surrogate, modulates Ca2+ responses in rat hepatocytes. FASEB J. 21, 1481-1491.

116. Rowe et al. (2006), A high-throughput microfluidic assay for SH2 domain-containing inositol 5-phosphatase-2. Assay Drug Develop. Technol. 4(2), 175-183.

117. U.S. Pat. No. 6,703,215 by Erneux et al.

118. U.S. Pat. No. 6,936,452 by Erneux et al.

119. U.S. Pat. No. 7,094,546 by Erneux et al.

120. International Patent Application Publication No. WO 02/069890.

121. United States Patent Application Publication NO. US 2004/0205831 A1 by Sleeman et al.

122. Weisz et al. (2000). Overexpression of frequenin, a modulator of phosphatidyl inositol 4-kinase, inhibits biosynthetic delivery of an apical protein in polarized madindarby canine kidney cells. J. Biol. Chem. 275(32): 24341-24347.

123. Hendrickes et al. (1999). Yeast homologue of neuronal frequenin is a regulator of phosphatidyl inositol-4-OH kinase. Nat. Cell Biol. 1(4):234-241.

124. Varnai and Balla. (1998). Visualization of phosphoinositides that bind pleckstrin homology domains: calcium agonist-induced dynamic changes and relationship to myo-[3H] inositol-labeled phosphoinositide pools. J. Cell Biol. 143(2):501-510.

125. Jonenning et al. (2004). Biochem. J. 382(Pt. 2):687-694.

126. DiPaolo et al. (2002). Decreased synaptic vesicle recycling efficiency and cognitive defects in amphiphysin 1 knockout mice. Neuron 33(5): 789-804.

127. Landman et al. (2006). Presenilin mutants linked to familial Alzheimer's Disease cause an imbalance in phosphoinositol 4,5 bisphosphate metabolism. Proc. Natl. Acad. Sci. U.S.A. 103(51):19524-19529.

128. Yang and Boss. (1994). Regulation of phosphatidylinositol 4-kinase by the protein activator PIK-A49. J Biol. Chem. 269(5):3852-7.

129. Yang et al. (1993). Purification and characterization of a phosphatidylinositol 4-kinase activator in carrot cells. J Biol. Chem. 268(1):392-8.

130. Yang and Boss. (1994). Archives of Biochemistry and Biophysics. 313(1):112-119.

Various publications are cited herein, the contents of which are hereby incorporated by reference in their entireties.

What is claimed is:

1. A method of treating Alzheimer's disease comprising administering, to a person in need thereof, an effective amount of an agent that increases neuronal levels of phosphoinositol 4,5 biphosphate, wherein the agent is KU-55933.

* * * * *